(12) United States Patent
Yao et al.

(10) Patent No.: US 11,492,373 B2
(45) Date of Patent: Nov. 8, 2022

(54) NUCLEANT ENHANCING NUCLEATION OF A PROTEIN CRYSTAL AND PROTEIN CRYSTALLIZATION METHOD WITH THE SAME

(71) Applicant: NATIONAL UNIVERSITY CORPORATION HOKKAIDO UNIVERSITY, Hokkaido (JP)

(72) Inventors: Min Yao, Sapporo (JP); Long Li, Sapporo (JP)

(73) Assignee: NATIONAL UNIVERSITY CORPORATION HOKKAIDO UNIVERSITY, Hokkaido (JP)

(*) Notice: Subject to any disclaimer, the term of this patent is extended or adjusted under 35 U.S.C. 154(b) by 82 days.

(21) Appl. No.: 17/079,739

(22) Filed: Oct. 26, 2020

(65) Prior Publication Data

US 2021/0130400 A1 May 6, 2021

(30) Foreign Application Priority Data

Oct. 31, 2019 (JP) .............................. JP2019-198549
Oct. 8, 2020 (JP) .............................. JP2020-170450

(51) Int. Cl.
- *C30B 29/56* (2006.01)
- *C07K 1/30* (2006.01)
- *B01J 19/10* (2006.01)
- *C07D 401/14* (2006.01)

(52) U.S. Cl.
CPC .............. *C07K 1/306* (2013.01); *B01J 19/10* (2013.01); *C07D 401/14* (2013.01)

(58) Field of Classification Search
CPC .. C30B 7/08; C30B 7/14; C30B 29/54; C30B 29/56; C07D 401/14; B01J 19/10; C07K 1/306
See application file for complete search history.

(56) References Cited

U.S. PATENT DOCUMENTS

| | | | | |
|---|---|---|---|---|
| 8,288,535 | B2* | 10/2012 | Fujita | C09K 19/40 544/181 |
| 2004/0062691 | A1* | 4/2004 | Haushalter | C30B 7/00 422/245.1 |
| 2005/0209377 | A1* | 9/2005 | Padwa | C08K 5/34 524/99 |
| 2006/0154052 | A1* | 7/2006 | Waffenschmidt | H05K 1/165 428/323 |
| 2010/0130652 | A1* | 5/2010 | Padwa | C08K 5/0083 524/101 |
| 2012/0135442 | A1* | 5/2012 | Reddy | C12N 9/2462 530/370 |
| 2018/0236122 | A1* | 8/2018 | Xiao | A61L 15/26 |

OTHER PUBLICATIONS

Sasa et al "Spontaneously resolved chiral interpentrating 3-D nets with two different zinc coordination polymers", J. Am Chem Soc 2001 vol. 123 pp. 10750-10751.*

(Continued)

*Primary Examiner* — Robert M Kunemund
(74) *Attorney, Agent, or Firm* — Wenderoth, Lind & Ponack, L.L.P.

(57) ABSTRACT

A balanced-lattice-ledge nucleant having ledge inducing local densification of proteins and a balanced-lattice inducing self-organized crystal packing. Using this balanced-lattice-ledge nucleant enhances nucleation of protein crystals.

15 Claims, 11 Drawing Sheets
(8 of 11 Drawing Sheet(s) Filed in Color)

(56) References Cited

OTHER PUBLICATIONS

Hayes et a., "the cyrstalline sponge method: a systematic study of the reproducibility of simple aromatic molecule encapsulation and guest-host interactions", Crystal Growth and Design, 2016 16 3465-3472.*
Wim G. J. Hol, "Structural genomics for science and society", Nature Structural Biology, 7, pp. 964-966, Nov. 2000.
Peter W. Rose et al., "The RCSB Protein Data Bank: views of structural biology for basic and applied research and education", Nucleic Acids Research, vol. 43, D345-D356, 2015.
Selva Kumari et al., "A structural biology perspective on bioactive small molecules and their plant targets", Current Opinion in Plant Biology, 14, pp. 480-488, 2011.
Yuta Suzuki et al., "Self-assembly of coherently dynamic, auxetic, two-dimensional protein crystals", Nature, vol. 533, pp. 369-373, May 19, 2016.
Alexander E. S. Van Driessche et al., "Molecular nucleation mechanisms and control strategies for crystal polymorph selection", Nature, vol. 566, pp. 89-94, Apr. 5, 2018.
Pieter Rein ten Wolde et al., "Enhancement of Protein Crystal Nucleation by Critical Density Fluctuations", Science, vol. 277, pp. 1975-1978, Sep. 26, 1997.
Emilie M. Pouget, et al., "The Initial Stages of Template-Controlled $CaCO_3$ Formation Revealed by Cryo-TEM", Science, vol. 323, pp. 1455-1458, Mar. 13, 2009.
Archan Dey et al., "The role of prenucleation clusters in surface-induced calcium phosphate crystallization", Nature Materials, vol. 9, pp. 1010-1014, Dec. 2010.
Peter G. Vekilov, "Nucleation", Crystal Growth & Design Perspective, vol. 10, pp. 5007-5019, 2010.
Koji Harano et al., "Heterogeneous nucleation of organic crystals mediated by single-molecule templates", Nature Materials, vol. 11, pp. 877-881, Oct. 2012.
Denis Gebauer et al., "Pre-nucleation clusters as solute precursors in crystallisation", Chem. Soc. Rev., 43, pp. 2348-2371, 2014.
Tomoya Yamazaki et al., "Two types of amorphous protein particles facilitate crystal nucleation", Proc. Natl. Acad. Sci., vol. 114, No. 9, pp. 2154-2159, 2017.
James F. Lutsko, "How crystals form: A theory of nucleation pathways", Sci. Adv., 5, eaav7399, Apr. 5, 2019.
Fabrice Gorrec, "The MORPHEHS protein crystallization screen", Journal of Applied Crystallography, 42, pp. 1032-1042, 2009.
Yusuke Tominaga et al., "Promotion of protein crystal growth by actively switching crystal growth mode via femtosecond laser ablation", Nature Photonics, vol. 10, pp. 723-726, Nov. 2016.
Gen Sazaki et al., "Novel coupling effects of the magnetic and electric fields on protein crystallization", Journal of Crystal Growth, 262, pp. 499-502, 2004.
Walter Littke et al., "Protein Single Crystal Growth under Microgravity", Science, vol. 225, pp. 203-204, Jul. 13, 1984.
Alexander McPherson et al., "Heterogeneous and Epitaxial Nucleation of Protein Crystals on Mineral Surfaces", Science, vol. 239, No. 4838, pp. 385-387, Jan. 22, 1988.
Igor Nederlof et al., "A Straightforward and Robust Method for Introducing Human Hair as a Nucleant into High Throughput Crystallization Trials", Crystal Growth & Design, 11, pp. 1170-1176, 2011.
Efrem Curcio et al., "Influence of the Structural Properties of Poly (vinylidene fluoride) Membranes on the Heterogeneous Nucleation Rate of Protein Crystals", J. Phys. Chem. B, vol. 110, No. 25, pp. 12438-12445, 2006.
Seth A. Darst et al., "Epitaxial growth of protein crystals from two-dimensional crystals on lipid layers", Current Opinion in Structural Biology, 5, pp. 640-644, 1995.
Simona Fermani et al., "Protein crystallization on polymeric film surfaces", Journal of Crystal Growth, 224 pp. 327-334, 2001.
Emmanuel Saridakis et al., "Protein crystallization facilitated by molecularly imprinted polymers", Proc. Natl. Acad. Sci. U.S.A., vol. 108, No. 27, pp. 11081-11086, Jul. 5, 2011.
Naomi E. Chayen et al., "Experiment and theory for heterogeneous nucleation of protein crystals in a porous medium", Proc. Natl. Acad. Sci., vol. 103, No. 3, pp. 597-601, Jan. 17, 2006.
Eugenia Pechkova et al., "Langmuir-Blodgett nanotemplates for protein crystallography", Nature Protocols, vol. 12, No. 12, pp. 2570-2589, 2017.
David Turnbull et al., "Nucleation Catalysis", Indusuial and Engineering Chemistry, vol. 44, No. 6, 1292-1298, Jun. 1952.
Akiyoshi Nakamura et al., "Ammonia Channel Couples Glutaminase with Transamidase Reactions in GatCAB", Science, vol. 312, pp. 1954-1958, Jun. 30, 2006.
Ken Yao et al., "Two-Dimensional Molecular Space with Regular Molecular Structure", Langmuir, vol. 24, No. 1, pp. 302-309, 2008.
Xiao-Ping Zhou et al., "A High-Symmetry Coordination Cage from 38- or 62-Component Self-Assembly", Journal of the American Chemical Society, 134, pp. 8042-8045, 2012.
Xiao-Ping Zhou et al., "Polyhedral Metal-Imidazolate Cages: Control of Self-Assembly and Cage to Cage Transformation", Journal of the American Chemical Society, 135, pp. 16062-16065, 2013.
Kyo Sung Park et al., "Exceptional chemical and thermal stability of zeolitic imidazolate frameworks", Proc. Natl. Acad. Sci., vol. 103, No. 27, pp. 10186-10191, Jul. 5, 2006.
Shohei Matsuzaki et al., "Networked-Cage Microcrystals for Evaluation of Host-Guest Interactions", Journal of the American Chemical Society, 136, pp. 17899-17901, 2014.
Masaki Kawano et al., "A Selective Instant Synthesis of a Coordination Network and Its Ab Initio Powder Structure Determination", Angew. Chemie Int. Ed., 47, 1269-1271, 2008.
Weichuo Pan et al., "Origin of Anomalous Mesoscopic Phases in Protein Solutions", J. Phys. Chem. B, vol. 114, No. 22, pp. 7620-7630, 2010.
C. Leong Ng et al., "Conformational flexibility and molecular interactions of an archaeal homologue of the Shwachman-Bodian-Diamond syndrome protein", BMC Structural Biology, 9, 32, 2009.
Christina L. Brown et al., "Template-Directed Assembly of a de Novo Designed Protein", J. Am. Chem. Soc., 124, pp. 6846-6848, 2002.
Paul Roach et al., "Surface Tailoring for Controlled Protein Adsorption: Effect of Topography at the Nanometer Scale and Chemistry", J. Am. Chem. Soc., 128, pp. 3939-3945, 2006.
Harley Pyles et al., "Controlling protein assembly on inorganic crystals through designed protein interfaces", Nature, vol. 571, pp. 251-256, Jul. 11, 2019.
Phillip W. Carter et al., "Nanoscale Surface Topography and Growth of Molecular Crystals: The Role of Anisotropic Intermolecular Bonding", J. Am. Chem. Soc., vol. 116, No. 3, pp. 944-953, 1994.
J. Willard Gibbs, "On the Equilibrium of Heterogeneous Substances", Am. J. Sci. s3-16, pp. 441-458, 1878.
Tian Hui Zhang et al., "How Does a Transient Amorphous Precursor Template Crystallization", J. Am. Chem. Soc., 129, pp. 13520-13526, 2007.
Makoto Fujita et al., "Palladium(0)/LiCl Promoted Cross-Coupling Reaction of (4-Pyridyl)stannanes and Aromatic Bromides: Easy Access to Poly(4-pyridyl)-Substituted Aromatics", Tetrahedron Letters, vol. 36, No. 29, pp. 5247-5250, 1995.
Akihiko Tsuji et al., "Identification and Characterization of a 25 kDa Protein That Is Indispensable for the Efficient Saccharification of *Eisenia bicyclis* in the Digestive Fluid of *Aplysia kurodai*", PLoS One, 12, e0170669, pp. 1-22, Jan. 27, 2017.
Yodai Taguchi et al., "Evaluation of acceptor selectivity of *Lactococcus lactis* ssp. *lactis* trehalose 6-phosphate phosphorylase in the reverse phosphorolysis and synthesis of a new sugar phosphate", Bioscience, Biotechnolology, and Biochemistry, vol. 81, No. 8, pp. 1512-1519, 2017.
Yosuke Tajika et al., "Crystal Stucture of Hypothetical Protein PH0828 From *Pyrococcus horikoshii*", Proteins: Structure, Function, and Bioinformatics, 57, pp. 862-865, 2004.
Wolfgang Kabsch, "XDS", Acta Crystallographica Section D Biological Crystallography, 66, pp. 125-132, 2010.

(56) References Cited

OTHER PUBLICATIONS

George M. Sheldrick, "Experimental phasing with SHELXC/D/E: combining chain tracing with density modification", Acta Crystallographica Section D Biological Crystallography, 66, pp. 479-485, 2010.

Paul D. Adams et al., "*PHENIX*: a comprehensive Python-based system for macromolecular structure solution", Acta Crystallographica Section D Biological Crystallography, 66, pp. 213-221, 2010.

Paul Emsley et al., "*Coot*: model-building tools for molecular graphics", Acta Crystallographica Section D Biological Crystallography, 60, pp. 2126-2132, 2004.

Takayuki Uchihashi et al., "Guide to video recording of structure dynamics and dynamic processes of proteins by high-speed atomic force microscopy", Nature Protocols, vol. 7, No. 6, pp. 1193-1206, 2012.

* cited by examiner

[Figure 1]
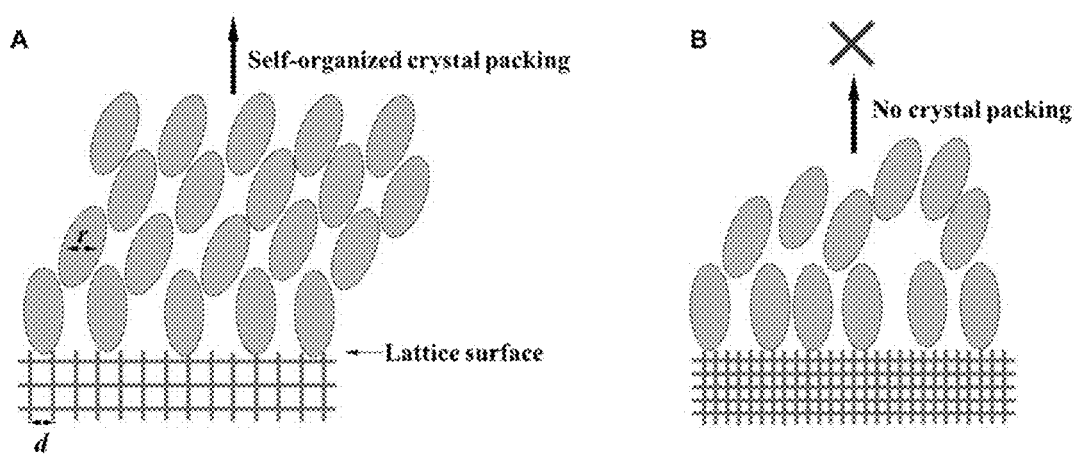

[Figure 2]
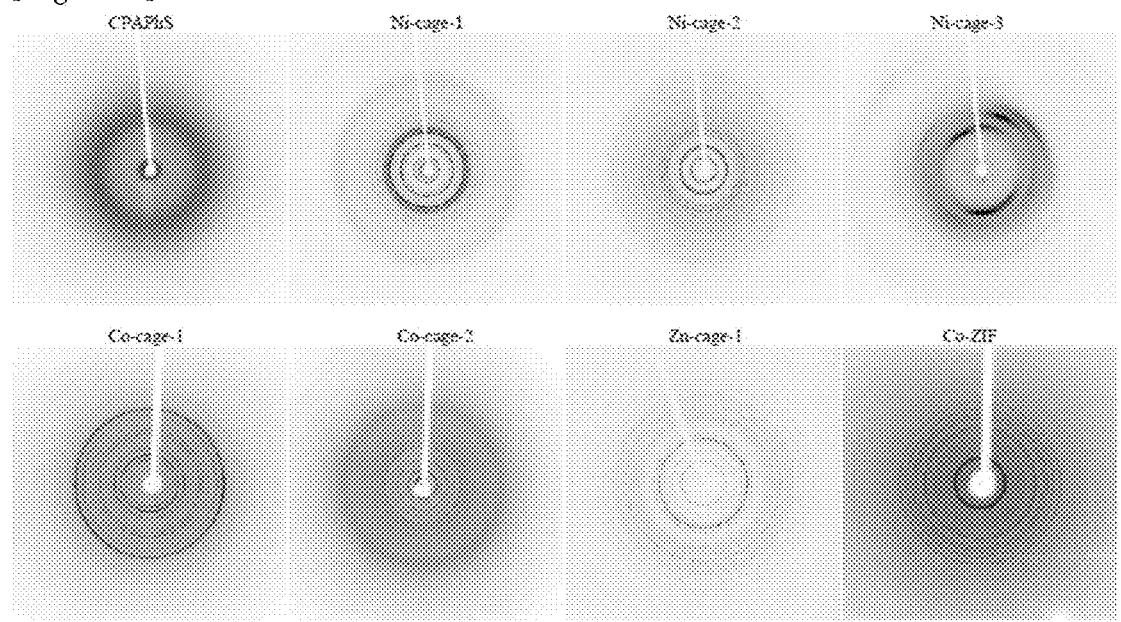

[Figure 3]
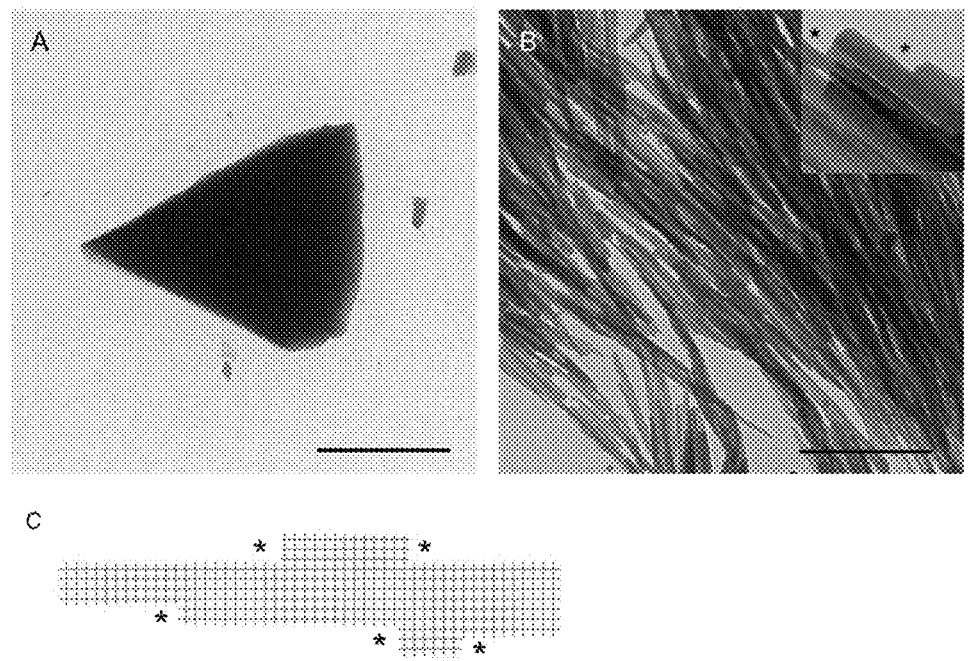

[Figure 4]
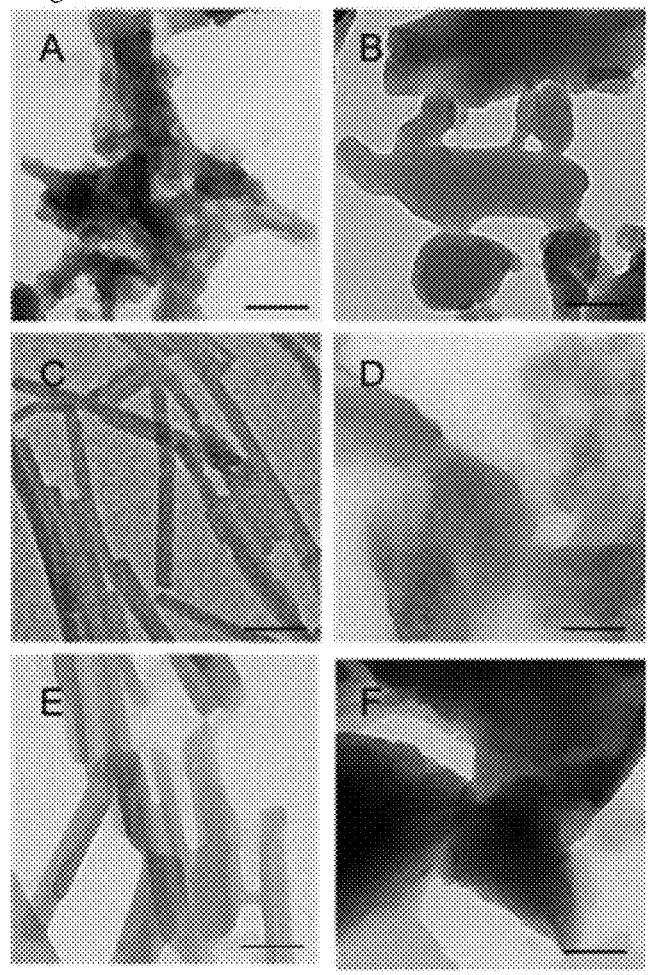

[Figure 5]
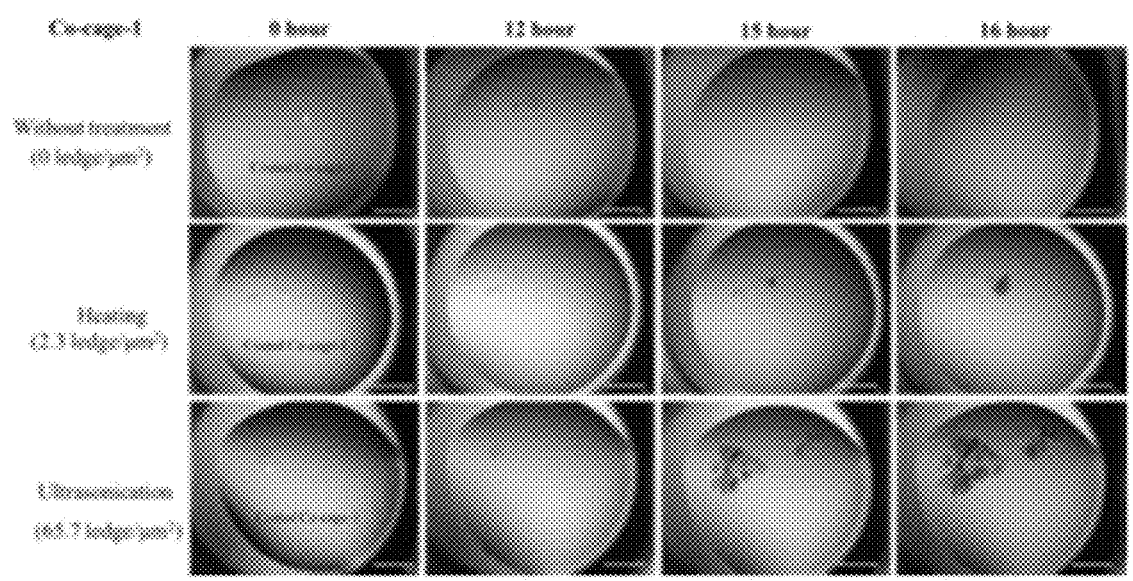

[Figure 6]
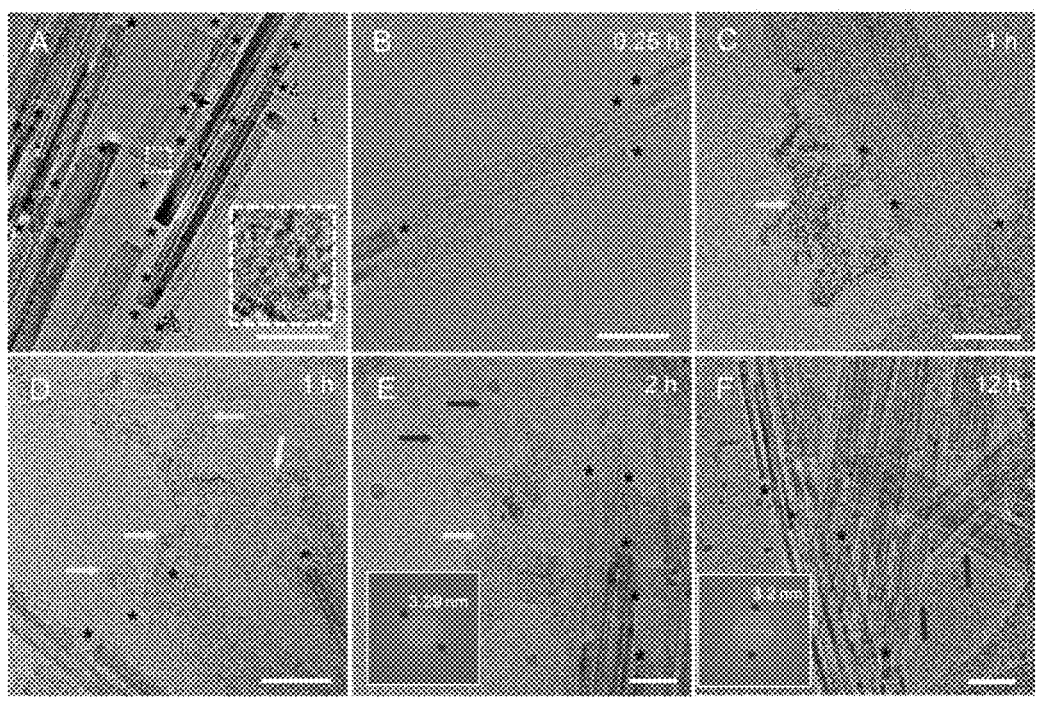

[Figure 7]
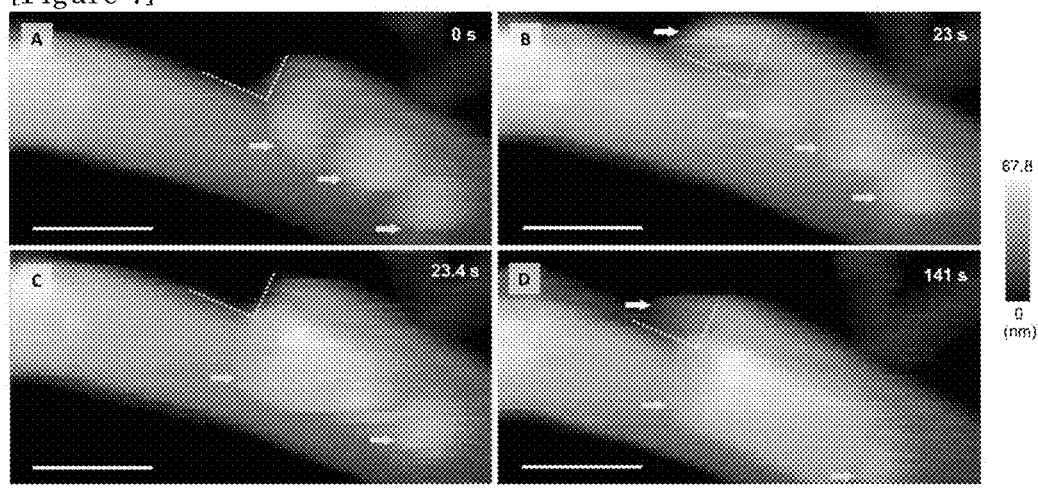

[Figure 8]
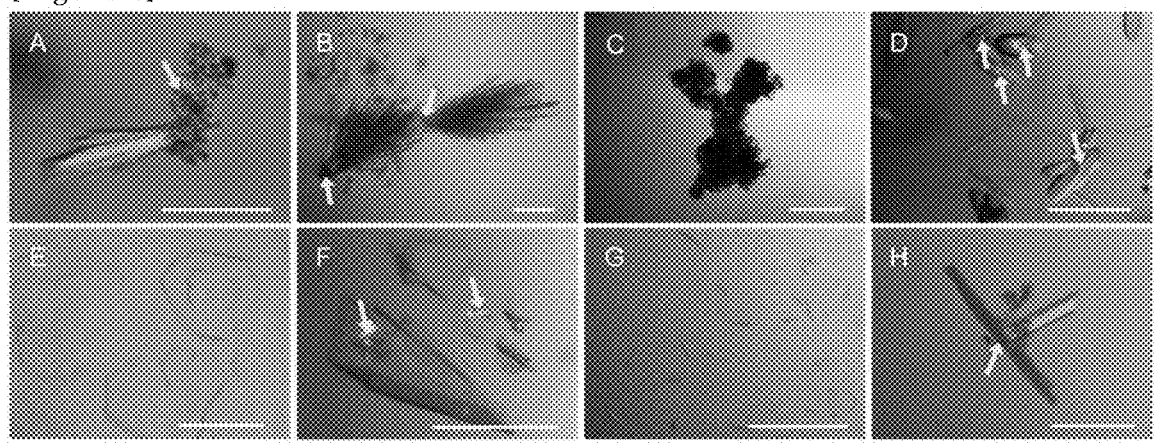

[Figure 9]
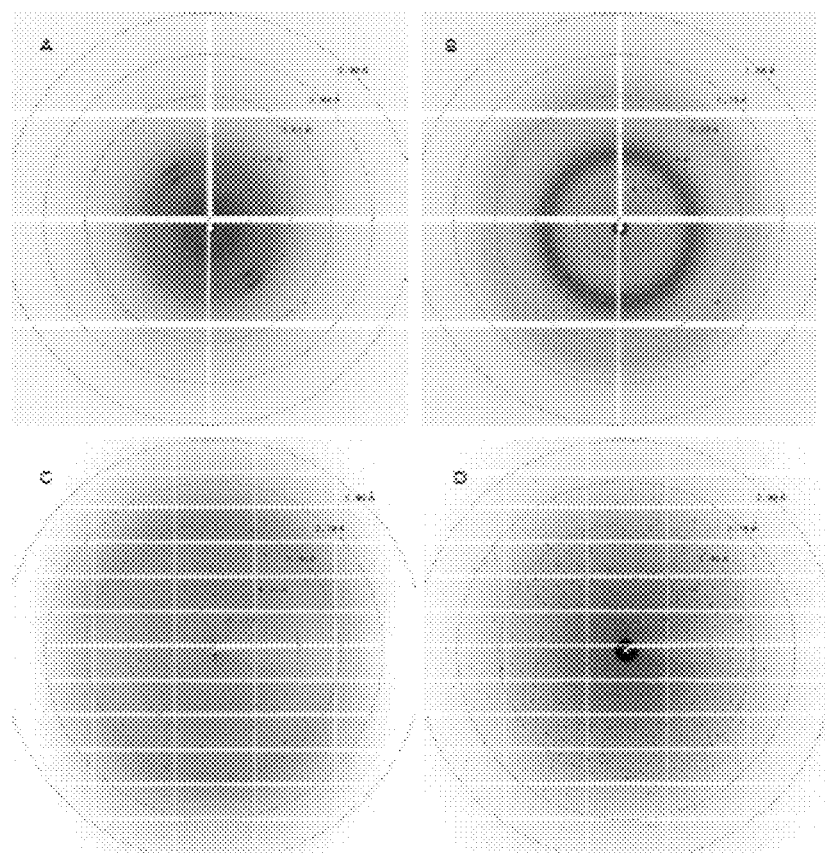

[Figure 10]
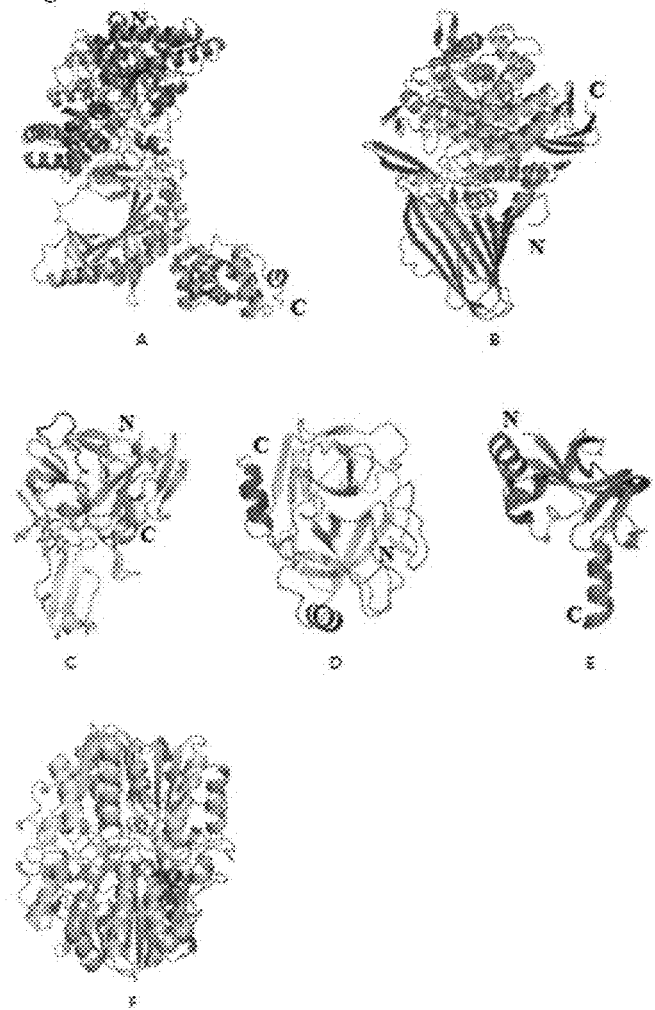

[Figure 11]
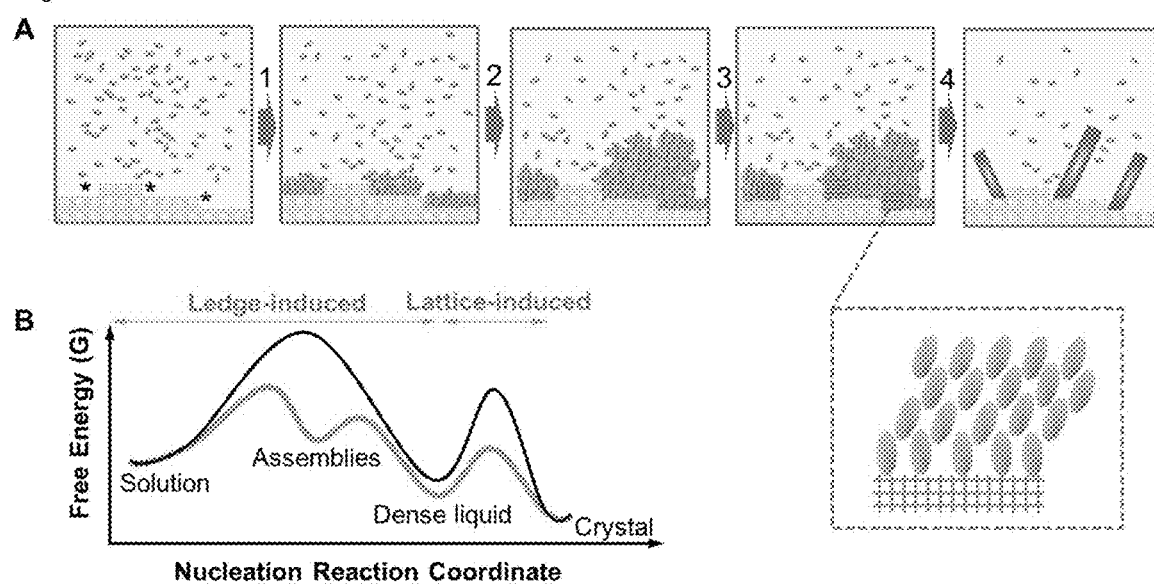

NUCLEANT ENHANCING NUCLEATION OF A PROTEIN CRYSTAL AND PROTEIN CRYSTALLIZATION METHOD WITH THE SAME

TECHNICAL FIELD

The present invention relates to a nucleant enhancing nucleation of a protein crystal. More specifically, the present invention provides a nucleant having a structure that induces a locally-dense liquid phase (high density liquid phase) of proteins and self-organized crystal packing.

BACKGROUND ART

Unlike inorganic molecules, the nucleation of protein crystals is a low-occurrence and uncontrollable solution-to-crystalline phase transition, mainly due to the morphologic complexity of protein molecules such as irregular size and shape, variable charge characteristics, and instability. The irregularity (difficulty) in nucleation (crystallization) of protein crystals adversely affects the development of protein crystallography and its application in the fields of biology, medicine and bio-agriculture, and pharmaceutical technology [Non-patent documents 1 to 4].

Previous studies on protein crystal nucleation in a solution and small molecule organic materials, colloids, polymer and biominerals, have demonstrated the existence of a nucleation zone in solubility phase diagram (crystallization diagram), and proposed two pathways of nucleation: direct nucleation and two-step phase transition. In the case of direct nucleation, primary multimers of molecules have already self-assembled as a crystalline state-like fiber [Non-patent document 5], while two-step phase transition is characterized by liquid-liquid phase separation and liquid-crystalline phase transition [Non-patent documents 6 to 13].

These findings guided to develop approaches for crystallizing target proteins. Besides providing chemical and physical factors (screening kits [Non-patent document 14], laser radiation [Non-patent document 15], magnetic/electric field [Non-patent document 16], microgravity [Non-patent document 17], etc.), nucleants such as natural minerals [Non-patent document 18] and horse or human hair [Non-patent document 19], are adapted to provide the foreign surface for triggering the heterogeneous nucleation of protein crystals. Moreover, surfaces of materials are further designed to synthesize a nucleant which enhances protein crystallization. These design strategies focus on surface morphology [Non-patent documents 20], lattice structure (lattice match between protein crystal and nucleant) [Non-patent document 21], and surface adsorption through charged surfaces [Non-patent document 22], molecularly imprinted polymers [Non-patent document 23], porous materials [Non-patent document 24], and protein thin films [Non-patent document 25].

Although surface engineering has led to superior designs and productions for nucleants, the development of versatile and effective nucleants is still challenging. This is because the most effective surface morphology and lattice structure and a mechanism by which a protein molecule is crystallized on a surface (Solution—crystalline phase transition) are poorly understood.

RELATED DOCUMENT

Non-Patent Document

[Non-patent document 1]
Hol, W. G. J. Structural genomics for science and society. Nat. Struct. Mol. Biol. 7, 964 (2000).
[Non-patent document 2]
Rose, P. W. et al. The RCSB Protein Data Bank: views of structural biology for basic and applied research and education. Nucleic Acids Res. 43, D345-D356 (2015).
[Non-patent document 3]
Kumari, S. & van der Hoorn, R. A L. A structural biology perspective on bioactive small molecules and their plant targets. Curr. Opin. Plant Biol. 14, 480-488 (2011).
[Non-patent document 4]
Suzuki, Y. et al. Self-assembly of coherently dynamic, auxetic, two-dimensional protein crystals. Nature 533, 369-373 (2016).
[Non-patent document 5]
Van Driessche, A. E. S. et al. Molecular nucleation mechanisms and control strategies for crystal polymorph selection. Nature 556, 89-94 (2018).
[Non-patent document 6]
Wolde, P. R. ten & Frenkel, D. Enhancement of Protein Crystal Nucleation by Critical Density Fluctuations. Science 277, 1975-1978 (1997).
[Non-patent document 7]
Pouget, E. M. et al. The Initial Stages of Template-Controlled CaCO3 Formation Revealed by Cryo-TEM. Science 323, 1455-1458 (2009).
[Non-patent document 8]
Dey, A. et al. The role of prenucleation clusters in surface-induced calcium phosphate crystallization. Nat. Mater. 9, 1010-1014 (2010).
[Non-patent document 9]
Vekilov, P. G. Nucleation. Cryst. Growth Des. 10, 5007-5019 (2010).
[Non-patent document 10]
Harano, K. et al. Heterogeneous nucleation of organic crystals mediated by single-molecule templates. Nat. Mater. 11, 877-881 (2012).
[Non-patent document 11]
Gebauer, D., Kellermeier, M., Gale, J. D., Bergstrom, L. & Colfen, H. Pre-nucleation clusters as solute precursors in crystallisation. Chem. Soc. Rev. 43, 2348-71 (2014).
[Non-patent document 12]
Yamazaki, T. et al. Two types of amorphous protein particles facilitate crystal nucleation. Proc. Natl. Acad. Sci. 114, 2154-2159 (2017).
[Non-patent document 13]
Lutsko, J. F. How crystals form: A theory of nucleation pathways. Sci. Adv. 5, eaav7399 (2019).
[Non-patent document 14]
Gorrec, F. The MORPHEUS protein crystallization screen. J. Appl. Crystallogr. 42, 1035-1042 (2009).
[Non-patent document 15]
Tominaga, Y. et al. Promotion of protein crystal growth by actively switching crystal growth mode via femtosecond laser ablation. Nat. Photonics 10, 723-726 (2016).
[Non-patent document 16]
Sazaki, G., Moreno, A. & Nakajima, K. Novel coupling effects of the magnetic and electric fields on protein crystallization. J. Cryst. Growth 262, 499-502 (2004).

[Non-patent document 17]
LITTKE, W. & JOHN, C. Materials: Protein Single Crystal Growth Under Microgravity. Science (80-.). 225, 203-204 (1984).

[Non-patent document 18]
Mcpherson, A. & Shlichta, P. Heterogeneous and Epitaxial Nucleation of Protein Crystals on Mineral Surfaces. Science 239, 385-387 (1988).

[Non-patent document 19]
Nederlof, I. et al. A Straightforward and Robust Method for Introducing Human Hair as a Nucleant into High Throughput Crystallization Trials. Cryst. Growth Des. 11, 1170-1176 (2011).

[Non-patent document 20]
Curcio, E., Fontananova, E., Di Profio, G. & Drioli, E. Influence of the structural properties of poly(vinylidene fluoride) membranes on the heterogeneous nucleation rate of protein crystals. J. Phys. Chem. B 110, 12438-12445 (2006).

[Non-patent document 21]
Darst, S. A. & Edwards, A. M. Epitaxial growth of protein crystals from two-dimensional crystals on lipid layers. Curr. Opin. Struct. Biol. 5, 640-644 (1995).

[Non-patent document 22]
Fermani, S., Falini, G., Minnucci, M. & Ripamonti, A. Protein crystallization on polymeric film surfaces. J. Cryst. Growth 224, 327-334 (2001).

[Non-patent document 23]
Saridakis, E. et al. Protein crystallization facilitated by molecularly imprinted polymers. Proc. Natl. Acad. Sci. U.S.A 108, 11081-11086 (2011).

[Non-patent document 24]
Chayen, N. E., Saridakis, E. & Sear, R. P. Experiment and theory for heterogeneous nucleation of protein crystals in a porous medium. Proc. Natl. Acad. Sci. 103, 597-601 (2006).

[Non-patent document 25]
Pechkova, E. & Nicolini, C. Langmuir-Blodgett nanotemplates for protein crystallography. Nat. Protoc. 12, 2570-2589 (2017).

[Non-patent document 26]
Turnbull, D. & Vonnegut, B. Nucleation Catalysis. Ind. Eng. Chem. 44, 1292-1298 (1952).

[Non-patent document 27]
Nakamura, A. Ammonia Channel Couples Glutaminase with Transamidase Reactions in GatCAB. Science 312, 1954-1958 (2006).

[Non-patent document 28]
Yao, K. et al. Two-Dimensional Molecular Space with Regular Molecular Structure. Langmuir 24, 302-309 (2008).

[Non-patent document 29]
Zhou, X.-P. et al. A High-Symmetry Coordination Cage from 38- or 62-Component Self-Assembly. J. Am. Chem. Soc. 134, 8042-8045 (2012).

[Non-patent document 30]
Zhou, X.-P., Wu, Y. & Li, D. Polyhedral Metal-Imidazolate Cages: Control of Self-Assembly and Cage to Cage Transformation. J. Am. Chem. Soc. 135, 16062-16065 (2013).

[Non-patent document 31]
Park, K. S. et al. Exceptional chemical and thermal stability of zeolitic imidazolate frameworks. Proc. Natl. Acad. Sci. 103, 10186-10191 (2006).

[Non-patent document 32]
Matsuzaki, S., Arai, T., Ikemoto, K., Inokuma, Y. & Fujita, M. Networked-Cage Microcrystals for Evaluation of Host-Guest Interactions. J. Am. Chem. Soc. 136, 17899-17901 (2014).

[Non-patent document 33]
Kawano, M., Haneda, T., Hashizume, D., Izumi, F. & Fujita, M. A Selective Instant Synthesis of a Coordination Network and Its Ab Initio Powder Structure Determination. Angew. Chemie Int. Ed. 47, 1269-1271 (2008).

[Non-patent document 34]
Pan, W., Vekilov, P. G. & Lubchenko, V. Origin of Anomalous Mesoscopic Phases in Protein Solutions. J. Phys. Chem. B 114, 7620-7630 (2010).

[Non-patent document 35]
Ng, C. L. et al. Conformational flexibility and molecular interactions of an archaeal homologue of the Shwachman-Bodian-Diamond syndrome protein. BMC Struct. Biol. 9, 32 (2009).

[Non-patent document 36]
Brown, C. L., Aksay, I. A., Saville, D. A. & Hecht, M. H. Template-Directed Assembly of a de Novo Designed Protein. J. Am. Chem. Soc. 124, 6846-6848 (2002).

[Non-patent document 37]
Roach, P., Farrar, D. & Perry, C. C. Surface Tailoring for Controlled Protein Adsorption: Effect of Topography at the Nanometer Scale and Chemistry. J. Am. Chem. Soc. 128, 3939-3945 (2006).

[Non-patent document 38]
Pyles, H., Zhang, S., De Yoreo, J. J. & Baker, D. Controlling protein assembly on inorganic crystals through designed protein interfaces. Nature 571, 251-256 (2019).

[Non-patent document 39]
Carter, P. W., Hillier, A. C. & Ward, M. D. Nanoscale Surface Topography and Growth of Molecular Crystals: The Role of Anisotropic Intermolecular Bonding. J. Am. Chem. Soc. 116, 944-953 (1994).

[Non-patent document 40]
Gibbs, J. W. On the equilibrium of heterogeneous substances. Am. J. Sci. s3-16, 441-458 (1878).

[Non-patent document 41]
Tian, H. Z. & Xiang, Y. L. How does a transient amorphous precursor template crystallization. J. Am. Chem. Soc. 129, 13520-13526 (2007).

[Non-patent document 42]
Fujita, M. Palladium(0)/LiCl Promoted Cross-Coupling Reaction of (4-Pyridyl)stannanes and Aromatic Bromides: Easy Access to Poly(4-pyridyl)-Substituted Aromatics. Tetrahedron Lett. 36, 5247-5250 (1995).

[Non-patent document 43]
Tsuji, A., Kuwamura, S., Shirai, A. & Yuasa, K. Identification and Characterization of a 25 kDa Protein That Is Indispensable for the Efficient Saccharification of Eisenia bicyclis in the Digestive Fluid of Aplysia kurodai. PLoS One 12, e0170669 (2017).

[Non-patent document 44]
Taguchi, Y., Saburi, W., Imai, R. & Mori, H. Evaluation of acceptor selectivity of Lactococcus lactis ssp. lactis trehalose 6-phosphate phosphorylase in the reverse phosphorolysis and synthesis of a new sugar phosphate. Biosci. Biotechnol. Biochem. 81, 1512-1519 (2017).

[Non-patent document 45]
Tajika, Y. et al. Crystal structure of hypothetical protein PH0828 from Pyrococcus horikoshii. Proteins Struct. Funct. Bioinforma. 57, 862-865 (2004).

[Non-patent document 46]
Kabsch, W. XDS. Acta Crystallogr. Sect. D Biol. Crystallogr. 66, 125-132 (2010).

[Non-patent document 47]
Sheldrick, G. M. (2010) Experimental phasing with SHELXC/D/E: combining chain tracing with density modification. Acta Cryst. D66, 479-485
[Non-patent document 48]
Adams, P. D. et al. PHENIX: A comprehensive Python-based system for macromolecular structure solution. Acta Crystallogr. Sect. D Biol. Crystallogr. 66, 213-221 (2010).
[Non-patent document 49]
Emsley, P. & Cowtan, K. Coot: Model-building tools for molecular graphics. Acta Crystallogr. Sect. D Biol. Crystallogr. 60, 2126-2132 (2004).
[Non-patent document 50]
Uchihashi, T., Kodera, N. & Ando, T. Guide to video recording of structure dynamics and dynamic processes of proteins by high-speed atomic force microscopy. Nat. Protoc. 7, 1193-1206 (2012).

DISCLOSURE OF THE INVENTION

Problem to be Solved by the Invention

The nucleation of protein crystals is a low-occurrence and uncontrollable solution-to-crystalline phase transition that impacts protein crystallography and its application in biology, medicine, bio-agriculture, and material science. The surface of a nucleant plays an important role in heterogeneous nucleation, but the design of effective nucleants is limited by a poor understanding of nucleation mechanism on their surfaces.

Means for Solving the Problem

The present inventors studied a nucleation mechanism of protein crystallization on a surface of a nucleant to demonstrate that balanced-lattice-ledge (BLL) surfaces greatly enhance the nucleation of protein crystals. Using cryo-transmission electron microscopy and high-speed atomic force microscopy to visualize the nucleation process of BLL, the present inventors clarified the role of BLL in solution-to-crystalline phase transition. Whilst the ledge (shelf) gathers protein assemblies to form a dense liquid phase which becomes a nucleation-precursor, the balanced-lattice (a lattice in which the lattice distance is balanced to accommodate the size of a range of protein molecules.) induces the regular-arrangement of protein molecules in the nucleation-precursor to initiate self-assembled crystal packing.

Effects of the Invention

In order to prove an effect of BLL on nucleation, a BLL nucleant was applied to 13 samples, including a membrane protein and hard-to-crystallize proteins. As a result, 11 samples were successfully crystallized and among the 11 samples, eight structures were solved and the crystal resolution of two proteins was improved, which demonstrate an enhancing effect of BLL on protein crystallization.

As above, these findings clarified by the present inventors about a heterogeneous nucleation mechanism further leads to the design of the most effective and novel nucleants, thereby development in applications to the field of protein crystallography as well as the fields of life science and material science is also expected.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1
Scheme of how the lattice surface of the nucleant triggers the nucleation of protein crystals: (A) Lattice distance (d) balanced with the size of the protein molecule (r) led to the molecular regular-arrangement which facilitates self-organized crystal packing of nucleation. (B) No crystal packing are formed because too many shifts of molecular arrangement are caused due to the unbalance between d and r.

FIG. 2
Powder diffraction patterns of eight candidate nucleants.

FIG. 3
TEM images of nucleants and definition of balanced-lattice-ledge: (A) The block shaped Ni-cage-3, and (B) The lamina shaped Co-cage-1. The inset is a magnified image, in which black star indicates the ledge on the surface. The scale bars represent 1 (C) shows the model of lattice-ledge in which the ledge (black star) consists of two intersecting planes when two thin film-like crystals are layered and lattice (blue gridding) is exposed on the surface of the plane.

FIG. 4
TEM Images of candidate nucleants: The ledge exists in A: CPAPhs, C; Co-cage-2, and E; Zn-cage-1, but not exists in B: Ni-cage-2, and D: Ni-cage-3, F: Co-ZIF. The all scale bars represent 100 nm.

FIG. 5
Crystallization of GatCAB with Co-cage-1 in different ledge density: All the scale bars represent 500 m. Yellow arrows marked Co-cage-1.

FIG. 6
Cryo-TEM images of the heterogeneous nucleation and growth of lysozyme crystal from BLL surface of Co-cage-1: (A) BLL-abundant Co-cage-1 which is uniformly dispersed in water and shows a lamina shape. The inset is a magnified image of the lattice-structure. (B)-(F) show heterogeneous nucleation and crystal growth in a time series (0.25, 1, 2, and 12 h). No changes around Co-cage-1 was observed within 0.25 h after the addition of the protein sample (B), whereas a protein dense liquid phase formed around the Co-cage-1 after 1 h (C)-(D). After 2 h, lysozyme crystals had grown from the interface between the dense liquid phase and Co-cage-1 at the ledge sites (E). Growth of lysozyme crystals from the BLL surface of Co-cage-1 was observed after 12 h, in parallel with the disappearance of the dense liquid phase (F). Black stars indicate the ledge sites on the surface. Yellow and blue arrows indicate a dense liquid phase, and lysozyme crystal, respectively. The green triangle represents the nucleation site. The insets in (E) and (F) show fast Fourier transform, indicating the crystallinity of lysozyme crystals. The scale bars represent 100 nm.

FIG. 7
The process of dense liquid phase formation on a ledge observed by HS-AFM: (A) Around a ledge site, three protein assemblies have attached on the Co-cage-1 surface (time=0 s). (B) Protein molecules have gathered and formed a new assembly, as indicated by the white arrow at the ledge site. The growth of the new assembly has reached its maximum length within 23 s. (C) The new assembly has detached from the ledge and merged with two adjacent assemblies within 0.4 s. (D) Another new protein assembly has regrown continuously from the ledge (white arrow) which subsequently contributes assembly-merging and formation of dense liquid phase. Protein assemblies are indicated by yellow arrows, and the ledge is marked by white dashed lines. The scale bar represents 50 nm in all images.

FIG. 8

Photos of protein crystals grown with/without Co-cage-1: Crystals of GatCAB (A) and EHEP (B) formed from the surface of Co-cage-1. (C) A mass of trypsin crystals formed on the surface of Co-cage-1 in the absence of substrates or inhibitors. Co-cage-1 were covered by trypsin crystals. (D) The crystals of PH0828 nucleated by Co-cage-1, which is inside the protein crystal. The crystals of Tre6PP were grown in the absence (E) and presence (F) of Co-cage-1. The crystallization of ychN without (G) and with (H) Co-cage-1. All crystals were grown in 1-2 weeks at 20° C. Yellow arrows show the position of Co-cage-1 particles. The scale bar represents 0.5 mm in all images.

FIG. 9

The diffraction patterns of Tre6PP and ycnN crystals: The diffraction patterns of Tre6PP crystal, which crystallized without Co-cage-1 (A) and with Co-cage-1 (B). The diffraction patterns of Complexi crystal, which crystallized without Co-cage-1 (C) and with Co-cage-1 (D).

FIG. 10

Determined structures which was crystallized by using Co-cage-1. All the structures are showed in ribbon mode. (A) The structure of GatCAB: Cat A, B, and C subunits are colored in blue, green and magenta, respectively. (B) The structure of Tre6PP. The helixes and sheet are colored in light-blue and magenta. (C) The structure of EHEP complexed with tannic acid (stick). Three domains are colored in orange, green and light-blue. (D), (E) and (F) are the structures of Trypsin, PH0828 and ychN, respectively.

FIG. 11

Proposed process of heterogeneous nucleation: (A) Schematic process of the heterogeneous nucleation of a crystal on BLL surface. Step 1: Formation of protein assemblies on the ledge sites of Co-cage-1. The dark stars indicate the BLL. Step 2: Formation of dense liquid phase via assembly-merging around the ledge site. Step 3: The nucleation of a crystal starts, where oriented proteins are regularly arranged on the lattice surface, inducing the formation of nanocrystalline particles (nuclears). The nanocrystalline particles are stabilized by the lattice surface on the ledge. Step 4: Growth of crystals inside the dense liquid. The dense liquid phase is consumed by nucleation and growth. (B) The free energy G of homogeneous (black line) and heterogeneous (orange line) nucleation processes. The two-step homogeneous nucleation of protein crystals was proposed by Peter G. Vekilov [Non-patent document 6], whereby the mesoscopic dense liquid phase is formed as the nucleation precursor. When the ledge and lattice induce heterogeneous nucleation, the formation of protein assemblies at the ledge site and the formation of the nucleus at the BLL decrease the energy barrier.

MODE FOR CARRYING OUT THE INVENTION

Whether through direct nucleation or the two-step phase transition pathway, the factors which trigger self-organized crystal packing are favorable for solution-to-crystalline phase transition. For example, investigations into the lattice structure of nucleants have benefited from using a lattice match in the nucleation of small molecules [Non-patent documents 26].

According to the concept of the conventional lattice match, a nucleant having lattice distance specific to a shape and size of a targeted protein to be crystallized should be prepared. Therefore, a wide variety of nucleants are required. Also, even if a nucleant matching with the shape and size was used, in some cases, the regular-arrangement of protein molecules could not be achieved.

The present inventors considered the complexity and variety of protein surfaces, and focused on the lattice structure due to its ability to induce regular-arrangement of protein molecules rather than lattice match. In this manner, the present inventors were able to conceive the balance of lattice distance for various proteins.

The balance between lattice distance of nucleants and molecule size affects the molecular-arrangement and thereby facilitates self-organized crystal packing of nucleation (FIG. 1A). In the case of imbalanced lattices, self-organized crystal packing is not triggered because there are too many shifts and they interfere with formation of regular molecular-arrangement (FIG. 1B).

Inspired by this concept, the present inventors designed and synthesized a series of candidate nucleants with different lattice distances. The assessment of the effect of lattice distance of candidate nucleants on the crystallization of two proteins, lysozyme and GatCAB (glutamine amidotransferase CAB) [Non-patent document 27] revealed that balanced-lattice distance and the ledges on the surface of nucleants are crucial for nucleation.

Additionally, in the present invention, the "lattice distance" of a nucleant means the largest value among lattice constants of the nucleant.

Furthermore, the process of nucleation at the balanced-lattice-ledge (BLL) was investigated using cryo-transmission electron microscopy (cryo-TEM) and high-speed atomic force microscopy (HS-AFM). The results revealed a heterogeneous nucleation mechanism in which the BLL plays a key role in nucleation.

Further, BLL nucleants prepared according the present invention was used to enable crystallization of 11 proteins (MW=11-110 kDa), including hard-to-crystallize samples and a membrane protein. Especially, it was confirmed that a BLL-abundant nucleant Co-cage-1 can significantly increase nucleation for protein crystallization.

The present invention provides, in the first aspect, a nucleant for crystallizing a protein. More specifically, the nucleant according to the present invention is a lamina-shaped flaky crystal of a metal complex in which 2,4,6-tris[4-pyridinyl]-1,3,5-triazine or 2,4,6-tris[4-(4-pyridinyl)phenyl]-1,3,5-triazine is coordinated with a central metal selected from cobalt and zinc, and which has an average ledge density of 10 ledges/$\mu m^2$ or more.

The metal complex in the nucleant according to the present invention is a metal complex in which 2,4,6-tris[4-pyridinyl]-1,3,5-triazine or 2,4,6-tris[4-(4-pyridinyl)phenyl]-1,3,5-triazine is coordinated with a cobalt divalent ion, or a metal complex in which 2,4,6-tris[4-pyridinyl]-1,3,5-triazine is coordinated with a zinc divalent ion.

Further, the protein crystallized with the nucleant according to the present invention is selected from a group consisting of GatCAB, EHEP, Tre6PP, trypsin, rhodopsin, Protein1, ychN, Protein2, PH0828, Annexin A2, and Lysozyme.

The nucleant according to the present invention is characterized in particular by being a lamina-shaped flaky crystal of a metal complex using a ledge structure.

The present invention provides, in the second aspect, a substrate to which the nucleant according to the present invention is attached.

The substrate according to the present invention is a crystallization plate having one or more wells. The number of well is not limited and a commercial 96-well microplate may be used. The nucleant according to the present invention is directly or indirectly attached to a surface of the substrate by adding an aqueous liquid (for example, a suspension or a slurry) into all or part of the one or more of wells, or by forming a coating layer of the nucleant on a surface of all or part of the one or more wells. The phrase "a nucleant is directly attached to a surface of a substrate" means that a nucleant itself is attached to the surface of a substrate to form a coating layer. The phrase "a nucleant is indirectly attached to a surface of a substrate" means that a nucleant itself is not attached to the surface of a substrate but a droplet or a layer of an aqueous liquid comprising the nucleant is formed on the surface of a substrate.

The present invention provides, in the third aspect, a method for crystallizing a protein. More specifically, the method of crystallization according to the present invention comprises at least placing the nucleant according to the present invention for crystallizing a protein onto a substrate to prepare a substrate to which the nucleant is attached; and contacting a protein with the nucleant.

In the method of crystallization according to the present invention, the nucleant may be attached to a substrate in a state of an aqueous liquid (for example, a suspension or a slurry) or a coating layer.

In the method of crystallization according to the present invention, a crystallization buffer comprising the protein is contacted with the nucleant attached to the substrate.

Further, in the method of crystallization according to the present invention, as above mentioned, a crystallization plate having one or more wells may be used as the substrate.

The present invention provides, in the fourth aspect, a kit for crystallizing a protein. More specifically, the crystallization kit according to the present invention comprises at least one or more kinds of nucleant according to the present invention for crystallizing a protein and a crystallization plate having one or more wells.

A nucleant having a lattice distance appropriate to a target protein to be crystallized is selected and attached on a surface of a crystallization plate to crystallize the protein on a surface of the nucleant.

EXAMPLES

Design and Selection of Nucleants

Initially, the present inventors used for experiments layered carboxylpropylamidephenylsilica (CPAPhS), a two-dimensional organic-inorganic hybrid material with a lattice distance of 5.2 Å, as a nucleant for crystallization. However, CPAPhS did not succeeded in crystallization (Table 1). Then, the present inventors considered that crystallization failed because the lattice distance of nucleants was balanced with a range of protein sizes (radius=25-75 Å, hydrodynamic radius hydrodynamic radius estimated based on statistical values (molecular weights) according to the Protein Data Bank (PDB)) and conceived that the lattice distance of nucleants should be sufficiently large unlike the conventional techniques (FIG. 1).

To increase lattice distance, the present inventions redesigned and synthesized the metal-organic frameworks (MOFs) as candidate nucleants with different lattice distances. These candidate nucleants are powdered materials in microcrystalline form with a range of lattice distances between 10 and 39 Å (Table 1; FIG. 2).

TABLE 1

Crystallization of lysozyme and GatCAB with/without 8 nucleants

| Candidate nucleants* | Metal + Compound | | Crystal parameters[b] | Ledge[c] | Crystallization[a] Lysozyme (r = 38 Å) | GatCAB (r = 49 Å) | GatCAB crystal parameters |
|---|---|---|---|---|---|---|---|
| — | — | — | — | — | No crystal | No crystal | — |
| CPAPhS[29] | — | — | 2D · P$_5$ mm<br>a = 5.2 Å | Has | No crystal | No crystal | — |
| Ni-cage-1[30] | Ni$^{2+}$ | (structure) | P432 cubic<br>a = 16.1 Å | No | No crystal | No crystal | — |
| Ni-cage-2[31] | Ni$^{2+}$ | (structure) | P43m cubic<br>a = 20.9 Å | No | No crystal | No crystal | — |
| Ni-cage-3 | Ni$^{2+}$ | (structure) | P4 tetragonal<br>a = b = 39.06 Å<br>c = 18.85 Å | No | No crystal | No crystal | — |
| Co-ZIF[32] | Co$^{2+}$ | (structure) | R3 trigonal<br>a = 20.9 Å<br>c = 15.8 Å | No | No crystal | No crystal | — |

TABLE 1-continued

Crystallization of lysozyme and GatCAB with/without 8 nucleants

| Candidate nucleants* | Metal + Compound | | Crystal parameters[b] | Ledge[c] | Lysozyme (r = 38 Å) | GatCAB (r = 49 Å) | GatCAB crystal parameters |
|---|---|---|---|---|---|---|---|
| Co-cage-1[33] | Co$^{2+}$ | 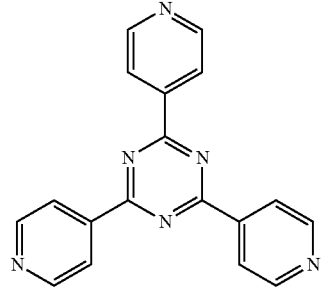 | Fm3m cubic a = 37.5 Å | Has | Crystals | Crystals | P2$_1$2$_1$2$_1$ a = 70.1 Å b = 91.0 Å c = 178.6 Å |
| Co-cage-2 | Co$^{2+}$ | 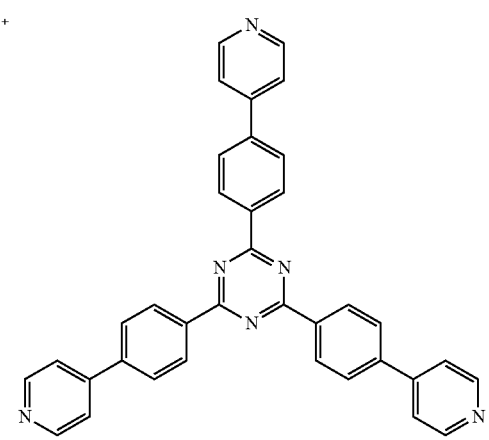 | P2$_1$ monoclinic a = 10.8 Å b = 16.7 Å c = 29.5 Å B = 94.3° | Has | Crystals | Crystals | P2$_1$2$_1$2$_1$ a = 70.5 Å b = 91.4 Å c = 178.6 Å |
| Zn-cage-1[34] | Zn$^{2+}$ | 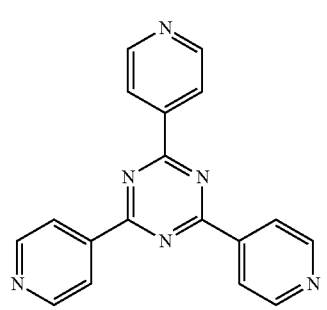 [SMILES: c1cc(-c2nc(-c3ccncc3)nc(-c3ccncc3)n2)ccn1] | O2c monoclinic a = 35.2 Å b = 14.7 Å c = 31.0 Å B = 103.1° | Has | Crystals | Crystals | P2$_1$2$_1$2$_1$ a = 71.0 Å b = 88.3 Å c = 182.1 Å |

[a]With the exception of CPAPhS, all candidate nucleants are 3D crystalline architectures composed of metal ions and compounds.
[b]Underlines mark the longest dimension of the unit cell.
[c]Here, the ledge is a kind of surface structure shown in FIG. 3C.
*A condition of no-lysozyme crystal formation was obtained using a low lysozyme concentration under well know crystallization conditions. The conditions of GatCAB crystallization are conditions where crystallization is not reproduced without previously-optimized seeding under.

To investigate the effect of lattice distance, crystallization of two model proteins: Lysozyme and GatCAB with/without eight candidate nucleants was performed. These two proteins were chosen as model proteins because their crystallization conditions are well optimized. This allows the efficiency of candidate nucleants to be readily distinguished under controlled conditions.

The results showed that the nucleation of lysozyme and GatCAB occurred with Co/Zn-cage-n (the indication "cage-n" collectively refers to cage-1 and cage-2. The same shall apply hereinafter.), but not with Ni-cage-n (e.g., dmax for Ni-cage-3 >30 Å), despite the lattice distances being almost similar to those of Co/Zn-cage-n (Table 1).

Next, TEM was used to visualize a variety of crystal morphologies of the candidate nucleants. TEM images showed different crystal morphologies of the candidate nucleants; Block shape in Ni-cage-n and lamina shape in Co/Zn-cage-n (FIGS. 3A and 3B, and FIG. 4).

Furthermore, a "ledge", a structure defined as the intersection of two plane resembling an L-shape from the side view (FIG. 3C), were observed on the surface of the lamina-shaped Co/Zn-cage-n and CPAPhS, but were absent from the block-shaped Ni-cage-n and Co-ZIF (FIG. 4).

The present inventors found that when a lamina-shaped flaky candidate nucleant: Co-cage-1 underwent a fracture process by applying a physical stimulus such as heating, ultrasonic radiation, etc. to form abundant ledges, it significantly increased nucleation probability and shortened nucleation time of lysozyme and GatCAB crystals. In particular, nucleants treated with ultrasonic irradiation so as to have an average ledge density of 60 ledges/μm² or more significantly increased the nucleation probability (Table 2, FIG. 5).

The lamina-shaped candidate nucleant CPAPhS failed to promote the nucleation of protein crystals, despite possessing ledges and lattice structure. This may be due to the fact that a lattice distance of the lattice of CPAPhS ($d_{max}$=5.2 Å) is too small to balance with a range of protein sizes (FIG. 1B).

Although the present invention is not limited with the following numerical range, the present inventors found that a nucleant having a lattice distance (d) preferably 0.3 to 3 times, further preferably 0.5 to 5 times the radius (r) of a protein size to be crystallized, or preferably 10 to 100 Å, further preferably 15 to 40 Å, and an average ledge density of 10 ledges/μm² or more, preferably 30 ledges/μm² or more, further preferably 50 ledges/μm² or more, yet further preferably 60 ledges/μm² or more, for example, 10 to 500 ledges/μm², preferably 30 to 200 ledges/μm², further preferably 50 to 150 ledges/μm² increases probability of protein nucleation.

The above results suggest that balanced-lattice and ledge function act cooperatively in the process of nucleation, leading the inventors to employ the term "Balanced-Lattice-Ledge (BLL)".

TABLE 2

Ledge densities of Co-cage-1, untreated, heated or ultrasonicated

| | Co-cage-1 | | | | | | | | |
|---|---|---|---|---|---|---|---|---|---|
| | Without treatment | | | Heating | | | Ultrasonication | | |
| | 1 | 2 | 3 | 1 | 2 | 3 | 1 | 2 | 3 |
| Total surface area[a] (μm²) | 2.639 | 3.467 | 6.587 | 33.154 | 13.611 | 40.827 | 3.136 | 3.47 | 0.772 |
| No. of Ledge[b] | 1 | 0 | 1 | 66 | 29 | 112 | 170 | 130 | 81 |
| Ledge density (ledge/μm²) | 0.38 | 0 | 0.15 | 2 | 2 | 3 | 54 | 38 | 105 |
| Average Ledge density (ledge/μm³) | | 0.18 | | | 2.3 | | | 65.7 | |

[a]The total surface areas are estimated from a surface area of a lamina-shaped flaky crystal in a TEM image using a Fuji Program (https://imagej.nih.gov/ij/docs/menus/analyze.html).
[b]The number of ledges is a sum counted in a TEM image.

Interestingly, as shown in Table 1, the structures of Co-cage-1, Co-cage-2 and Zn-cage-1 respectively belong to different space groups with different lattice-distances. However, all the GatCAB crystals nucleated by Co-cage-1, Co-cage-2, and Zn-cage-1 were formed in the same space group with similar unit cell dimensions (Tables 3, 4 and 5). These results demonstrate that the balanced-lattice surfaces of nucleants promote a self-organized crystal packing for crystal nucleation, but do not match with the crystal lattice of protein in the manner expected.

TABLE 3

Statistics of data colletion for GatCAB crystals nucleated with Co-cage-1

| | Co-cage-1-nucleated GatCAB crystals | | | |
|---|---|---|---|---|
| | Crystal 1 | Crystal 2 | Crystal 3 | Crystal 4 |
| Diffraction source | BL-1A, PF | | | |
| Wavelength (Å) | 1.000 | | | |
| Measurement Temperature (K) | 100 | | | |
| Oscillations (°) | 0.1 | | | |
| Exposure time per image (s) | 0.3 | | | |
| Space group | $P2_12_12_1$ | | | |
| a, b, c (Å) | 70.2, 91.0, 178.5 | 69.8, 91.1, 178.6 | 70.1, 91.0, 178.5 | 70.0, 90.8, 178.9 |
| Resolution range (Å) | 50-3.24 (3.43-3.24) | 50-2.72 (2.89-2.72) | 50-2.82 (2.99-2.82) | 50-2.72 (2.89-2.72) |

TABLE 3-continued

Statistics of data colletion for GatCAB crystals nucleated with Co-cage-1

| | Co-cage-1-nucleated GatCAB crystals | | | |
|---|---|---|---|---|
| | Crystal 1 | Crystal 2 | Crystal 3 | Crystal 4 |
| Multiplicity | 3.6 (3.2) | 3.5 (3.5) | 1.8 (1.8) | 3.6 (3.6) |
| Completeness (%) | 99.3 (97.3) | 99.2 (96.5) | 95.8 (92.7) | 99.5 (97.8) |
| $<I>/<\sigma(I)>$ | 9.1 (1.75) | 9.65 (1.65) | 5.97 (1.08) | 10.03 (1.92) |
| Rmeas[a] | 0.16 (0.82) | 0.12 (0.82) | 0.14 (0.70) | 0.12 (0.82) |

[a] $R_{meas} = \Sigma hkl[Nhkl/(Nhkl-1)]1/2\Sigma i \mid Ii(hkl) - <I(hkl)> \mid /\Sigma hkl\Sigma iIi(hkl)$, wherein $<I(hkl)>$ and Nhkl are the average intensity and the multiplicity of a set of equivalent reflections, respectively.

TABLE 4

Statistics of data colletion for GatCAB crystals nucleated with Co-cage-2

| | Co-cage-2-nucleated GatCAB crystals | | | |
|---|---|---|---|---|
| | Crystal 1 | Crystal 2 | Crystal 3 | Crystal 4 |
| Diffraction source | BL-1A, PF | | | |
| Wavelength (Å) | 1.000 | | | |
| Measurement Temperature (K) | 100 | | | |
| Oscillations (°) | 0.1 | | | |
| Exposure time per image (s) | 0.3 | | | |
| Space group | $P2_12_12_1$ | | | |
| a, b, c (Å) | 70.4, 91.0, 179.0 | 70.9, 91.6, 178.5 | 70.8, 91.4, 178.8 | 70.0, 91.6, 178.0 |
| Resolution range (Å) | 50-2.71 (2.88-2.71) | 50-2.22 (2.35-2.22) | 50-2.52 (2.67-2.52) | 50-2.12 (2.25-2.12) |
| Multiplicity | 3.5 (3.6) | 1.9 (1.9) | 3.6 (3.7) | 3.6 (3.6) |
| Completeness (%) | 99.6 (98.7) | 92.9 (88.3) | 99.4 (97.0) | 99.4 (97.1) |
| $<I>/<\sigma(I)>$ | 9.64 (1.68) | 8.68 (1.38) | 9.38 (1.46) | 14.41 (2.1) |
| Rmeas[a] | 0.14 (0.95) | 0.1 (0.78) | 0.12 (0.93) | 0.07 (0.66) |

[a] $R_{meas} = \Sigma hkl[Nhkl/(Nhkl-1)]1/2\Sigma i \mid Ii(hkl) - <I(hkl)> \mid /\Sigma hkl\Sigma iIi(hkl)$, wherein $<I(hkl)>$ and Nhkl are the average intensity and the multiplicity of a set of equivalent reflections, respectively.

TABLE 5

Statistics of data colletion for GatCAB crystals nucleated with Zn-cage-1

| | Zn-cage-1-nucleated GatCAB crystals | | | |
|---|---|---|---|---|
| | Crystal 1 | Crystal 2 | Crystal 3 | Crystal 4 |
| Diffraction source | BL-1A, PF | | | |
| Wavelength (Å) | 1.000 | | | |
| Measurement Temperature (K) | 100 | | | |
| Oscillations (°) | 0.1 | | | |
| Exposure time per image (s) | 0.3 | | | |
| Space group | $P2_12_12_1$ | | | |
| a, b, c (Å) | 72.0, 87.8, 182.3 | 70.9, 88.8, 181.9 | — | — |
| Resolution range (Å) | 71.0, 88.3, 182.1 | | — | — |
| Multiplicity | 50-4.02 (4.26-4.02) | 50-3.63 (3.85-3.63) | — | — |
| Completeness (%) | 6.5 (5.5) | 6.5 (6.4) | — | — |
| $<I>/<\sigma(I)>$ | 99.2 (95.9) | 99.5 (97.7) | — | — |
| Rmeas[a] | 6.15 (1.93) | 10.19 (2.195) | — | — |
| Oscillations (°) | 0.27 (0.80) | 0.15 (0.89) | — | — |

[a] $R_{meas} = \Sigma hkl[Nhkl/(Nhkl-1)]1/2\Sigma i \mid Ii(hkl) - <I(hkl)> \mid /\Sigma hkl\Sigma iIi(hkl)$, wherein $<I(hkl)>$ and Nhkl are the average intensity and the multiplicity of a set of equivalent reflections, respectively.

Heterogeneous Nucleation on the Surface of BLL-Abundant Co-Cage-1

To elucidate the mechanism of heterogeneous nucleation on the BLL surface of the nucleant, the present inventors used BLL-abundant Co-cage-1 to observe the crystallization of lysozyme. The observation results on the nucleation process by cryo-TEM and HS-AFM indicate that BLL is an important factor for the rapid rate and high probability of nucleation.

Using cryo-TEM, the present inventors observed the BLL surface and lattice-structure of Co-cage-1 clearly without a protein sample (FIG. 6A). 0.25 h after the addition of a protein sample to a crystallization buffer, protein assemblies or mesoscopic dense liquid phases were not observed, even around Co-cage-1 similar to the protein-free environment (FIG. 6B). After 1 h incubation, a higher contrast phase appeared around Co-cage-1, which extended from ledges with variable shapes and sizes (FIGS. 6C and 6D). Those formed by lysozyme molecules can be considered as a dense liquid phase [Non-patent documents 9, 34]. Lysozyme crystals were not observed at the 1 h time point. However, needle-like crystals appeared after 2 h of incubation, which grew from Co-cage-1, in parallel with a reduction of the dense liquid phase (FIGS. 6E and 6F). Furthermore, fast Fourier transform (FFT) of cryo-TEM images confirmed that the lattice distance of the needle-like crystals was compliant with the lattice constant of the a-axis in the P212121 space group of the lysozyme crystal. These crystals emanate from ledges and elongate toward a direction along an angle with Co-cage-1 (FIG. 6E). After 12 h, the dense liquid phase disappeared, and many needle-like crystals had grown from the BLL surface of Co-cage-1 (FIG. 6F).

Combining these observations, the process of crystallization on Co-cage-1 is initiated by the ledge promoting the formation of the dense liquid phase, which serves as a precursor of nucleation. Subsequently, the phase transition from the dense liquid phase to crystalline nucleus (nucleation) is induced by the lattice structure on ledge sites, followed by crystal growth.

That is, a nucleant for crystallizing a protein which shows an enhancing effect on nucleation is a lamina-shaped flaky crystal of a metal complex in which 2,4,6-tris[4-pyridinyl]-1,3,5-triazine represented by a general formula (1):

[Chemical formula 1]

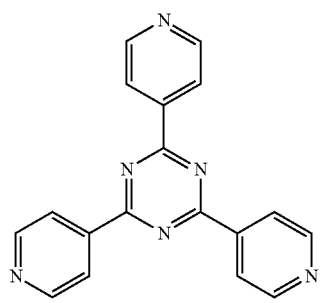

(1)

or 2,4,6-tris[4-(4-pyridinyl)phenyl]-1,3,5-triazine represented by a general formula (2):

[Chemical formula 2]

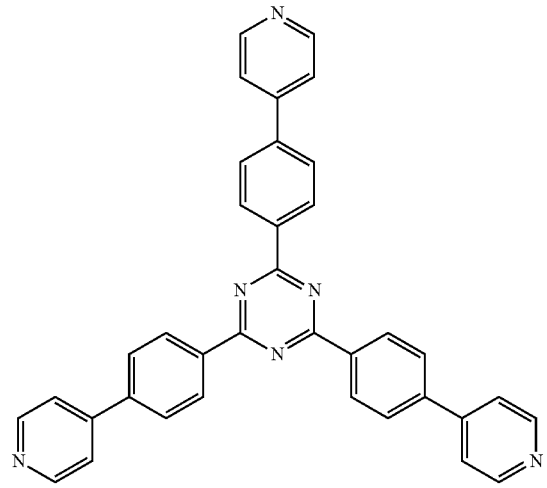 [SMILES: c1cc(-c2ccc(-c3nc(-c4ccc(-c5ccncc5)cc4)nc(-c4ccc(-c5ccncc5)cc4)n3)cc2)ccn1]

(2)

is coordinated with a central metal selected from cobalt and zinc, which has an average ledge density of 10 ledges/$\mu m^2$ or more.

The above metal complexes have a structure of linked three-dimensional structures (basket) in which any of the two types of triazine derivatives is coordinated with a cobalt ion ($Co^{2+}$) or a zinc ion ($Zn^{2+}$) as a central metal via nitrogen atoms of the pyridinyl groups of them.

The nucleant according to the present invention shows an enhancing effect on nucleation for crystallizing GatCAB and Lysozyme. Co-cage-1 shows an enhancing effect on nucleation for crystallizing any one of proteins selected from a group consisting of GatCAB, EHEP, Tre6PP, trypsin, rhodopsin, Protein1, ychN, Protein2, PH0828, Annexin A2, and Lysozyme.

Such a nucleant for crystallizing a protein may be produced by a production method comprising:
a metal complex preparation step for preparing a metal complex in which 2,4,6-tris[4-pyridinyl]-1,3,5-triazine represented by a general formula (1) or 2,4,6-tris[4-(4-pyridinyl)phenyl]-1,3,5-triazine represented by a general formula (2) is coordinated with a central metal selected from cobalt and zinc;
a crystallization step for crystallizing the metal complex obtained in the metal complex preparation step; and
a fracture step for fracturing the crystal of the metal complex obtained in the crystallization step by applying a physical stimulus.

The present inventors then employed HS-AFM to further investigate the process occurring at the ledges. Discerning the liquid-liquid phase separation and liquid-crystalline phase transition is problematic as nucleation events are a continuous phase transition process. As such, the present inventors gradually increased lysozyme concentration from 0.025 mg/ml to achieve a suitable condition for observation. At a concentration of 2.6 mg/ml (C/Cs=0.89), previously unclear liquid-liquid phase separation was observed at the ledge site (no crystal formed under this condition). A time series of HS-AFM images at a ledge site is shown in FIG. 7. Firstly, the ledge provides an active site for gathering protein molecules to form a new assembly (FIGS. 7A and 7B), followed by a detachment of the assembly from the ledge (FIGS. 7B and 7C). Secondly, detached assemblies merge with adjacent assemblies, which was accompanied by dynamic changes in both assembly size and shape (FIGS. 7C and 7D). Finally, dense liquid phase formation co-occurs with assembly-merging (FIG. 7D). The evolution of protein assemblies displays a growing-detaching-regrowth process with a growth rate of 1.44 nm/s at the ledge site (FIGS. 7A to 7D). This growing-detaching-regrowth process contributes to assembly-merging and dense liquid phase formation. In addition, the adjacency of the assemblies on the surface also provide useful points for assembly-merging during continuous growth.

General Applicability of BLL-Abundant Co-Cage-1 in Protein Crystallization

To evaluate general effectiveness of BLL nucleants in protein crystallization, the present inventors confirmed whether BLL-abundant Co-cage-1 induced crystallization for 12 proteins using commercial crystallization screening kits at 20° C. The molecular weight of these proteins ranges from 11 to 110 kDa, which covers more than 90% of the proteins deposited in PDB. Of the 12, one is a membrane protein and nine have proved difficult to crystallize (including not only samples that do not crystallize, but also samples that have poor reproducibility even if crystallize, and samples with poor crystalline quality that are difficult to analyze its structure due to lack of single crystal formation or low resolution. Then, the present inventors demonstrated that Co-cage-1 is a fairly effective nucleant for crystallizing various proteins.

With the exception of a protein, SBDS (Shwachman-Bodian-Diamond syndrome), Co-cage-1 facilitated the nucleation of all the proteins tested (Table 6). FIG. 8 shows that all the proteins were crystallized on the surface of Co-cage-1. Due to the nucleation effectiveness of Co-cage-1, the present inventors could find new crystallization conditions of GatCAB, EHEP, trypsin, rhodopsin, Protein1 and Annexin A2 (Table 6). The crystal formation of GatCAB and EHEP, which exhibit poor reproducibility according to the conventional crystallization techniques, exhibited reproducibility close to 100% using Co-cage-1 (Table 6, FIGS. 8A and 8B). Although Protein1 had not been previously crystallized, Co-cage-1 promoted the nucleation thereof. Similarly, crystals of trypsin have not been obtained at room temperature in the absence of substrates or inhibitors during initial crystallization screening. However, the crystals thereof were obtained in the presence of Co-cage-1. Co-cage-1 not only enhanced nucleation, but also improved the crystal quality (resolution) of Tre6PP and ychN from 3.3 and 3.4 Å to 1.54 and 1.9 Å, respectively (FIGS. 8E to 8H, and 9).

Amongst the 11 crystallized proteins, structures for eight proteins were determined and it was confirmed that those structures were not affected with Co-cage-1 (FIG. 10).

SBDS failed to crystallize even in the presence of co-cage-1. This may be due to the domain-flexibility architecture of SBDS [Non-patent document 35].

TABLE 6

Results of crystallization with/without Co-cage-1 for 12 proteins

| Protein | MW (kDa) | Problems in Crystallization | Hits[a] − | Hits[a] + | Advantages with Co-cage-1 | Space group | Structure determination[b] |
|---|---|---|---|---|---|---|---|
| GatCAB | 110 | Nonreproducible | 1/384 | 2/384 | Reproducible | $P2_12_12_1$ | 2.0 Å |
| EHEP | 25 | Nonreproducible | 1/96 | 2/96 | Reproducible | $P2_12_12_1$ | 1.15 Å |
| Tre6PP | 87 | Low resolution <3.3Å | 1/384 | 1/384 | High resolution | P1 | 1.54 Å |
| Trypsin | 24 | No crystal | 0/384 | 4/384 | Easy crystallization | $P2_12_12_1$ | 1.75 Å |
| Rhodopsin | 32[-4] | Low resolution <8.0Å | 10/96 | 12/96 | Easy crystallization | | On going |
| Protein1 | 54 | No crystal | 0/1536 | 6/192 | Easy crystallization 5 Å | | On going |
| yehN | 13[-6] | Low resolution <3.2Å | 4/384 | 5/384 | High resolution | $P2_12_12_1$ | 1.88 Å |
| Protein2 | 110 | Low resolution <4.0Å | 1/1 | 1/1 | High resolution | P62 | 3.6 Å |
| Annexin A2 | 39 | — | 3/192 | 6/192 | More conditions | $P2_1$ | On going |
| PH0828 | 15 | — | 1/384 | 1/384 | Same as normal | $P4_12_12$ | 3.0 Å |

TABLE 6-continued

Results of crystallization with/without Co-cage-1 for 12 proteins

| Protein | MW (kDa) | Problems in Crystallization | Hits[a] − | Hits[a] + | Advantages with Co-cage-1 | Space group | Structure determination[b] |
|---|---|---|---|---|---|---|---|
| Lysozyme | 14 | — | 8/96 | 13/96 | More conditions | P2₁2₁2₁ | 2.5 Å |
| SBDS | 29 | No crystal | 0/384 | 0/384 | No | — | — |

[a]Crystallization screening was carried out using the kits (96 conditions per kit) without (−) and with (+) Co-cage-1. Only the conditions resulting in protein crystals or crystallites are considered as hits and shown as the number of hits/number of conditions.
[b]The structures of each sample were determined at marked resolution using crystals obtained after optimizing the crystallization condition with Co-cage-1.
GatCAB, glutamine amidotransferase CAB;
EHEP, *Eisenia* hydrolysis enhancing protein;
Tre6PP, trehalose-6-phosphate phosphorylase;
Trypsin, a serine protease;
Rhodopsin, a photoreceptor protein;
Protein1, an Src-like nonreceptor tyrosine kinase;
ychN, a conserved hypothetical protein from *Escherichia coli*;
Protein2, a Calcium-regulated membrane-binding protein;
Annexin A2, a calcium-regulated membrane-binding protein;
PH0828, a hypothetical protein from *Pyrococcus horikoshii* OT3;
Lysozyme, N-acetylmuramide glycanhydrolase;
SBDS, Shwachman-Bodian-Diamond syndrome.

Discussion

In crystallization of a protein, the process of nucleation via self-organized crystal packing in protein crystallization is problematic. As such, the present inventors focused on developing an effective nucleant to induce molecular arrangement regularity, thereby improving self-organization in heterogeneous nucleation. The results reveal that lamina-shaped flaky BLL-abundant MOFs facilitate the heterogeneous nucleation of protein crystals, dramatically enhancing the success rate of protein crystallization necessary in structure determination.

The three nucleants tested nucleated GatCAB crystals in identical crystal form, and a BLL-abundant nucleant Co-cage-1 nucleated 11 different protein crystals. These results strongly imply that the lattice of the nucleant according to the present invention serves mainly as a guider of molecular ordering, rather than as a lattice match. Similar guidance properties of lattices is also observed in the process of protein adsorption [Non-patent documents 36 to 38]. Furthermore, the results of the crystallization experiments using the candidate nucleants indicate that the balanced-lattice distance impacts the guidance effect, as proposed in FIG. 1A (Table 1). In addition to the balanced-lattice, comparative experiments confirm that the ledge is also indispensable for nucleation (Table 1, FIG. 5). The anisotropic microcrystalline of nucleant MOFs seem to favor the formation of a lamina-shaped flake with a ledge structure on the surface [Non-patent document 39]. The control of the production of BLL nucleants should be further investigated through material science research.

The cryo-TEM and HS-AFM experiments reveal that ledges serve as active sites for producing and stabilizing protein assemblies, which leads to a two-step liquid-liquid phase separation via assembly-merging. Protein assembly-merging contributes to the formation of a nucleation-precursor, possibly due to a high local density of protein assemblies on the nucleant surface around the ledge site. Coupling the ledge with the balanced-lattice structure may order the molecular orientation, resulting in the initiation of self-organized crystal packing. Compared with homogeneous nucleation, this nucleation process may decrease the nucleation energy barrier of crystalline nuclei formation [Non-patent documents 40, 41].

These discoveries led the present inventors to propose a heterogeneous nucleation mechanism in which BLL-directed nucleation of protein crystals proceeds through four distinct steps (FIG. 11A). The ledge forms a protein assembly (Step 1). Accumulation and merging of these protein assemblies on the surface of the nucleants lead to the formation of the dense liquid phase (Step 2). The lattice structure on the BLL surface induces the regular-arrangement of protein molecules, resulting in self-organized crystal packing to form the crystalline nucleus from the interface between the BLL surface and the dense liquid (Step 3). Finally, the crystal grows through the further incorporation and addition of the dense liquid or protein molecules in solution (Step 4). Compared with homogeneous nucleation, the heterogeneous nucleation of BLL is more energy favorable due to the balanced-lattice-ledge directed multi-step nucleation mechanism (FIG. 11B).

This study has increased our understanding of the heterogeneous nucleation mechanism and will facilitate the design of effective nucleants for crystallizing proteins. In turn, this will advance the development of protein crystallography and its application in areas such as structural based binder/enzyme design and pharmaceutical technology.

Methods

Synthesis of Compounds and Nucleants

To prepare Co-cage-2, first, its chemical component 2,4,6-tris[4-(4-pyridinyl)phenyl]-1,3,5-triazine was synthesized. This synthesis was performed using a previously published procedure [Non-patent document 42] to characterize the product by use of 1H NMR and MALDI-TOF MS.

Synthesis of nucleants CPAPhS, Ni-cage-1, Ni-cage-2, Co-ZIF, Co-cage-1 and Zn-cage-1 and crystallization: These materials were synthesized using previously reported protocols [Non-patent documents 28, 30 to 33]. CPAPhS is a two-dimensional layered aminopropylsilica, whereas the others are MOF microcrystals. To a solution of 2,4,6-tris[4-pyridinyl]-1,3,5-triazine (4 mM, 9.0 L) in methanol is poured a solution containing Co(NCS)$_2$ at two equivalents of the aforementioned ligand (for example, 40 mM, 1.8 L) in methanol in all at once (for example, within 10 seconds) and vigorously stirred it. After stirring for 30 seconds, orange-colored crystalline power precipitated. This precipitate was filtered to obtain a microcrystalline of Co-cage-1. A solution of the ligand 2,4,6-tris[4-pyridinyl]-1,3,5-triazine (for example, 0.16 mmol) in a mixed solvent of nitrobenzen/methanol (for example, 32/4 mL) was poured in all at once into a 1.5-equivalent solution (for example, 8 mL) of $ZnBr_2$ (for example, 0.24 mmol) in methanol, resulting in precipitation of homogeneous crystalline powder. This precipitate was filtered to obtain a microcrystalline of Zn-cage-1.

Synthesis of Co-cage-2 crystal: A solution of 2,4,6-Tris [4-(4-pyridinyl)phenyl]-1,3,5-triazine (300 mg, 0.56 mmol) in o-dichlorobenzene (800 ml) and methanol (200 ml) was prepared in a 2 L PYREX® bottle. A solution of $Co(NCS)_2$ (8.57 mM, 200 ml) in methanol was added slowly whilst stirring. A suspended cotton-like precipitate appeared after 1 week of incubation. The resulting solution was allowed to stand for several months at room temperature, and red single crystals formed on the surface of the precipitate.

Synthesis of Ni-cage-3 single crystal: A mixture of 4-formylimidazole (200 mg, 2.08 mmol), $Ni(NO_3)_2 \cdot 6H_2O$ (360 mg, 1.24 mmol) and methanol (20 mL) was heated and stirred in a 50 ml flask at 84° C. After 1 h reflux, 2-Phenethylamine (774 mg, 6.39 mmol) was added following precipitation and color change. The mixture was stirred for 24 h and filtrated through a 0.2 μm PTFE membrane. The solution was then transferred to a 50 ml conical centrifuge tube (Falcon™) and kept at room temperature. A large single crystal appeared after incubation for 1 several months.

Treatment of the Nucleants

The nucleants were washed using the same solvent used in their synthesis, and harvested by filtration. The fresh nucleants were heated at 60° C. for 3 weeks, which led to complete removal of the solvent molecules from the microporous channels in the material.

Heating of Co-cage-1: 5 mg of Co-cage-1 powder was suspended in 1 ml water and then incubated at 95° C. for 1 h. The mixture was centrifuged and washed in water before coating it on a crystallization plate.

Ultrasonication of Co-cage-1: 5 mg of Co-cage-1 powder was suspended in 1 ml water, and then disrupted for 1 min using an ultrasonic disruptor (TOMY, UD-211) at an output level of 2.5. The mixture was centrifuged and washed in water before coating it on a crystallization plate.

Comparison of ledge density: TEM images of Co-cage-1 (untreated, heated, and ultrasonic-treated) were taken using a Hitachi H-7650 at 80 kV with a magnification of ×5,000. For calculating ledge density, TEM images of each treated Co-cage-1 were used to count the ledge number manually before integrating the observed surface area of Co-cage-1 using Fiji software (https://imagej.nih.govhj/docs/menus/analyze.html). The value of the observed ledge density is calculated by dividing the ledge number by the surface area. The numbers of ledges and the observed surface areas of Co-cage-1 in each image, and the calculated ledge densities are summarized in Table 2.

Powder X-Ray Diffraction of Candidate Nucleants

The crystallinity of the nucleants was characterized by X-ray powder diffraction patterns (XRD) from an in-house x-ray machine (Rigaku MicroMax-007HF rotating-anode X-ray generator equipped with the Rigaku RAXIS IV++ image plate detector), using Cu-Kα radiation (X=1.540562 Å, 40 kV, 20 mA) as the X-ray source. Samples were placed in quartz capillaries, which were exposed to the incident X-ray beam.

TEM Observations of Nucleants

All nucleants were treated by ultrasonication. Samples for TEM measurements were prepared by placing a drop of nucleant suspended in water on a polymer-coated copper grid, which were then dried in air at room temperature. TEM observations were performed using a Hitachi H-7650, operated at 80 kV or the JEM-2100F TEM system (JEOL, Japan) at an acceleration voltage of 200 kV.

Preparation of Proteins

Chicken egg-white lysozyme (L6876) and bovine pancreatic trypsin (T7309) are commercially available from Sigma-Aldrich. Eisenia hydrolysis enhancing protein (EHEP) [Not-patent document 43], trehalose-6-phosphate phosphorylase (Tre6PP) [Not-patent document 44], Rhodopsin, Protein1, ychN, Protein2, and Annexin A2 were provided by collaborators. Glutamine amidotransferase CAB (GatCAB), PH0828, and human Shwachman-Bodian-Diamond syndrome (SBDS) protein were expressed and purified using previously described protocols [Not-patent documents 27, 35, 45]. Protein solubilization buffers for the respective proteins are as follows:

lysozyme: Milli Q water;
Trypsin: 25 mM HEPES pH 7.0, 5 mM $CaCl_2$);
EHEP: 20 mM NaOAc pH 6, 100 mM NaCl;
Tre6PP: 20 mM MES-NaOH pH 6.0;
Rhodopsin; 5 mM Tris-HCl pH 8, 0.05% (w/v) dodecyl-beta-D-maltoside;
Protein1: 10 mM Tris-HCl pH 8.5, 25 mM NaCl, 5 mM DTT;
ychN: 10 mM Tris-HCl pH 6, 20% glycerol;
Protein2: 20 mM Bis-Tris pH 6.0;
Annexin A2: 20 mM Tris-HCl pH 7.5, 150 mM NaCl, 1 mM DTT, 5% glycerol;
GatCAB: 20 mM Tris-HCl pH 7.5, 100 mM NaCl, 10 mM $MgCl_2$, 10% (v/v) glycerol, 1 mM DTT;
PH0828:10 mM Tris-HCl pH 9; and
SBDS: 20 mM Tris-HCl (pH 7.5), 150 mM NaCl, 1 mM $MgCl_2$, 5% (v/v) glycerol.

Crystallization of Proteins

All crystallizations were performed using the sitting drop vapor diffusion method in 96-well plates (two pits/well) (MRC-2, SwissSci) at 20° C. To prevent the precipitation covering the surface of the nucleants and a subsequent loss of heterogeneous nucleation, protein concentrations were maintained at the level of no-precipitation occurrence in the crystallization drop when the drops were prepared.

Evaluation of nucleants on protein crystallization: Eight nucleants were coated onto one pit of each well of a crystallization plate separately by depositing and drying solutions containing the nucleants ($OD_{600}$=1.0). Lysozyme (10 mg/ml) and GatCAB (15 mg/ml) were used to assess crystallization in Crystallization buffer A (0.1 M sodium acetate pH 4.6, 2.0 M sodium chloride) and Crystallization buffer B (50 mM HEPES-NaOH pH 7.2, 26% (v/v) PEG-600, 5 mM $MgCl_2$, 3% MPD), respectively.

In the present invention, a "crystallization buffer" is different from the above protein solubilization buffer and is a buffer enhancing crystallization of a protein and containing a "precipitant" such as salts, for example, sodium chloride and ammonium sulfate, and polyethylene glycol. Appropriately selecting a type and a concentration of "precipitant" based on the properties of each protein, the solubility of the protein is reduced by the principle of salting out to form nuclei, and then a crystal grow.

Crystallization drops were prepared by mixing 1 μl of the protein sample and 1 μl of crystallization buffer (an external solution). The protein crystals were analyzed by optical microscopy and further confirmed using an in-house x-ray machine or beam lines from Synchrotron facilities PF (Photon Factory, Ibaraki, Japan) and SPring-8 (Harima, Japan).

Crystallization screening of proteins using Co-cage-1 coated crystallization plates: As above, Co-cage-1 microcrystals were coated onto one pit of a crystallization plate. For comparison, crystallization drops were added to two pits (with/without Co-cage-1) of each well under equivalent crystallization conditions. The drops were prepared by mixing 1 μl of protein sample and 1 μl of a solution (an external solution) of commercial crystallization kit JCSG core I-IV suites (96 conditions per kit) (Qiagen, US). Only for Rhodopsin, the drops were prepared by mixing 0.4 μl of protein with the same volume of a solution (an external solution) of commercial crystallization kit (MemGold) using the crystallization robot, Mosquito® (TTP LabTech, UK). Protein crystals were checked using optical microscopy, and further confirmed after 2 weeks using an in-house x-ray machine or beam lines from Synchrotron facilities PF and SPring-8. Positive crystallization results with/without coated Co-cage-1 were recorded as a "hit."

Optimization of crystal quality using Co-cage-1 powder: Co-cage-1 powder was directly added to the crystallization drop using a seeding tool (Hampton Research, US). The crystallization drops were prepared by mixing 1 μl of protein sample with 1 μl of reservoir solution.

Measurement of Lysozyme Solubility

The solubility of lysozyme crystals in a solution of 0.05 M sodium acetate pH 4.6, and 1 M sodium chloride was determined using a batch technique. This lysozyme crystal suspension was prepared in a PCR tube by dissolving the lysozyme crystals to achieve saturation. The PCR tubes were then incubated at 20° C. Lysozyme concentration was measured by UV absorption at 280 nm until the values were steady for three consecutive days. The concentration was determined by comparison with the standard curve. The supersaturation ratio is defined as C/Cs, where C is the concentration of lysozyme and Cs is the saturation concentration.

Data Collection and Structure Determination

Single crystal X-ray diffraction data for Ni-cage-3 and Co-cage-2 were collected using the aforementioned in-house X-ray machine. Diffraction data for the structure determination of proteins was collected at beamlines of the synchrotron facilities of the Photon Factory and SPring-8. Prior to data collection, the crystals were cryo-protected in their cryoprotectant solution (crystallization buffer containing 15-25% (v/v) glycerol), and then flash-cooled in a liquid nitrogen stream. All diffraction data for the protein crystals were indexed, integrated, scaled and merged by the XDS program [Non-patent document 46]. EHEP and ychN were analyzed by single-wavelength anomalous diffraction (SAD) of sulfur atoms and iodine atoms by using ShelxCDE and PHENIX_autosolve program [Non-patent documents 47, 48], while others were determined by the direct refinement or molecular replacement method (MR) using their published structure by using PHENIX_molrep [Non-patent document 48]. The structures were further refined with PHENIX_refine [Non-patent document 48], following manual model building/modifying using COOT [Non-patent document 49].

Optical Microscopic Observation of Nucleation

Time-lapse wide-field images were acquired with an automated inverted microscope (Olympus IX71). A Co-cage-1 single crystal or microcrystal was placed on the glass surface of the cell and aligned with its c-axis parallel to the focal plane. The crystal growth solution, which contained 25 mg/ml lysozyme, 0.05 M sodium acetate pH 4.6, and 1 M sodium chloride, was identical to that used in the experiments with HS-AFM. The growth solution was filtered using a syringe filter with a pore size of 0.2 μm before being sealed in the cell. The temperature of the cell was maintained at 20° C. using Peltier elements on the cell stage. The delay time between two successive frames was set at 1 min. Experiments were typically performed for 3 h.

Cryo-TEM Observation of Nucleation, Performed at Institute for Protein Research, Osaka University Preparation of grids with Co-cage-1 particles: To obtain suitably sized Co-cage-1 particles for cryo-TEM observation, the Co-cage-1 suspension was filtered through a 3-layer filter paper (No. 526, Toyo Roshi Kaisha Ltd., Tokyo, Japan) after ultrasonication. The Co-cage-1 filtrate was collected and condensed to a concentration of $OD_{600}$=0.19, then 0.3 μl of the solution was applied to the glow-discharged holey carbon grids (Quantifoil R0.6/1 Mo, 300 mesh). Excess solution was blotted with filter paper to ensure that the Co-cage-1 particles were located on the carbon films.

Crystallization on the grids with Co-cage-1 particles: Crystallization was conducted in a closed plastic box in which wet paper wiping rags (KimWipes, Kimberly Clark Corporation, USA) were placed on the wall to maintain high humidity and avoid sample drying. 10 μl drops of the crystallization buffer (0.05 M sodium acetate pH 4.2, and 1.75 M sodium chloride) containing 8.5 mg/ml lysozyme were pipetted one by one at four locations on top of a parafilm. Each of four grids with Co-cage-1 particles were then transferred onto the surface of the respective drops, where they floated due to surface tension of the drops. The grids were harvested after 0.25, 1, 2 and 12 h of crystallization at 20° C. The vitrification process was performed in Vitrobot Mark IV (FEI) under 95% humidity and at 20° C. The blotting force was set to 0 and blotting time to 10 s. The grids were transferred to liquid nitrogen and stored. The vitrified specimens were examined using FEI Titan Krios™ at 300 kV and the images were recorded on a Falcon III direct detection camera.

HS-AFM Observation of Nucleation Performed at Kanazawa University

The laboratory-built high-speed AFM was used in the tapping mode [Non-patent document 50]. The cantilever deflection was detected with an optical beam deflection detector, onto which a 0.8 mW, 670 nm red laser was mounted. The laser was focused onto the back side of the cantilever (Olympus: BL-AC10DS-A2) through a ×20 objective lens (Nikon: CFI Plan Fluor ELWD 20×C). The reflected laser from the cantilever was detected by a two-segmented PIN photodiode. The spring constant of the cantilever was ~100 pN/nm. The resonant frequency and the quality factor of the cantilever in liquid were ~500 kHz and ~2, respectively. An amorphous carbon tip was fabricated on the original AFM tip by electron beam deposition (EBD). The length of the additional AFM tip was ~500 nm, and the radius at the apex of the tip was ~4 nm. The free oscillation amplitude of the cantilever was ~1 nm, and the set-point amplitude was set to 90% of the free amplitude. Crystals of Co-cage-1 were anchored on the sample stage with a small amount of glue (SUPER-X, Cemedine Co. Ltd., Japan). After the sample stage was fixed using nail polish on the z-piezo of the HS-AFM scanner, the Co-cage-1 was rinsed with crystallization buffer consisting of 0.05 M sodium acetate pH4.6 and 1 M sodium chloride. After the capture of the Co-cage-1 surface, the buffer was replaced with crystallization buffers containing varying concentrations of lysozyme (0.025-25 mg/ml). This series of resuspensions increased the lysozyme concentration gradually, and enabled the observation of the nucleation process. All HS-AFM experiments were performed at 20° C.

INDUSTRIAL APPLICABILITY

With the usage of the balanced-lattice-ledge nucleant according to the present invention, protein crystals can be rapidly and efficiently nucleated, thus enabling crystallization of proteins which is difficult to analyze structures thereof due to low reproducibility or low resolution in the prior art. Further, since the use of the nucleant of the present invention does not have an effect of changing the crystal structure of the protein, the study of the protein can be enhanced. Therefore, it is industrial applicable not only for research in the field of life sciences, but also for industries such as pharmaceutical technology (dosage form) and production of biopolymers.

The invention claimed is:

1. A nucleant for crystallizing a protein, which is a lamina-shaped flaky crystal of a metal complex, in which 2,4,6-tris[4-pyridinyl]-1,3,5-triazine represented by a general formula (1):

[Chemical formula 1]

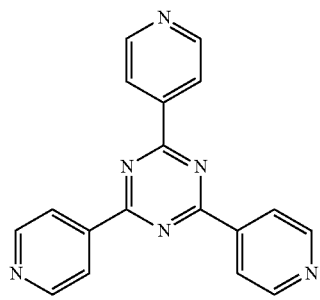

(1)

or 2,4,6-tris[4-(4-pyridinyl)phenyl]-1,3,5-triazine represented by a general formula (2):

[Chemical formula 2]

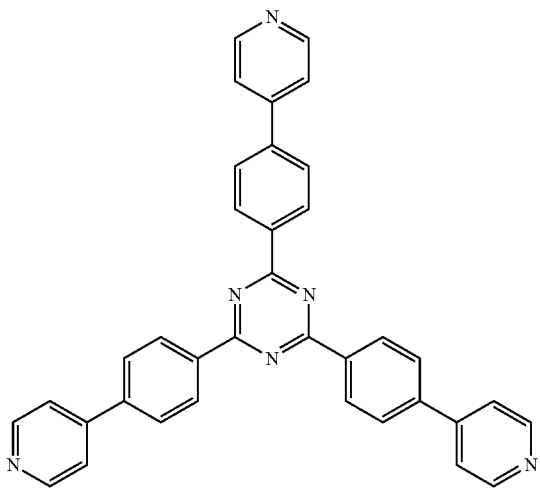

(2)

is coordinated with a central metal selected from cobalt and zinc,
which has an average ledge density of 10 ledges/$\mu m^2$ or more.

2. The nucleant according to claim 1, wherein the metal complex is a metal complex in which 2,4,6-tris[4-pyridinyl]-1,3,5-triazine or 2,4,6-tris[4-(4-pyridinyl)phenyl]-1,3,5-triazine is coordinated with a cobalt divalent ion, or a metal complex in which 2,4,6-tris[4-pyridinyl]-1,3,5-triazine is coordinated with a zinc divalent ion.

3. The nucleant according to claim 1, wherein the protein is a protein selected from a group consisting of GatCAB, EHEP, Tre6PP, trypsin, rhodopsin, Protein1, ychN, Protein2, PH0828, Annexin A2, and Lysozyme.

4. The nucleant according to claim 1, which is a lamina-shaped flaky crystal of a metal complex having a ledge structure.

5. A method for producing a nucleant for crystallizing a protein, comprising:
a metal complex preparation step for preparing a metal complex in which 2,4,6-tris[4-pyridinyl]-1,3,5-triazine represented by a general formula (1):

[Chemical formula 3]

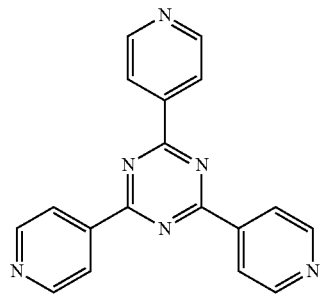

(1)

or 2,4,6-tris[4-(4-pyridinyl)phenyl]-1,3,5-triazine represented by a general formula (2):

[Chemical formula 4]

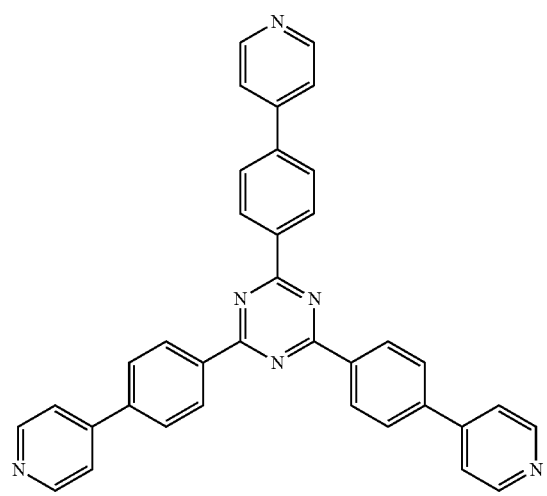

(2)

is coordinated with a central metal selected from cobalt and zinc;
a crystallization step for crystallizing the metal complex obtained in the metal complex preparation step,
wherein the metal complex preparation step and the crystallization step together comprising
adding a solution of a central metal selected from cobalt and zinc in methanol to a solution of 2,4,6-tris[4-pyridinyl]-1,3,5-triazine or 2,4,6-tris[4-(4- pyridinyl)phenyl]-1,3,5-triazine in methanol, nitrobenzene and/or dichlorobenzene to form a lamina-shaped flaky crystal of the metal complex in which 2,4,6-tris[4-pyridinyl]-1,3,5-triazine or 2,4,6-tris[4-(4-pyridinyl)phenyl]-1,3,5-triazine is coordinated with a cobalt divalent ion or a zinc divalent ion; and a fracture step for fracturing the crystal of the metal complex obtained in the crystallization step by applying a physical stimulus to make the average ledge density of the crystal of the metal complex to 10 ledges/$\mu m^2$ or more.

6. The method according to claim 5, wherein the physical stimulus is ultrasonic radiation.

7. A substrate, to which the nucleant for crystallizing a protein according to claim 1 is attached.

8. The substrate according to claim 7, which is a crystallization plate having one or more wells.

9. The substrate according to claim 8, wherein an aqueous liquid comprising a nucleant is added into all or part of the one or more of wells, or a coating layer of the nucleant is formed on a surface of all or part of the one or more wells.

10. A method for crystallizing a protein, comprising at least:

placing the nucleant for crystallizing a protein according to claim 1 onto a substrate to prepare a substrate to which the nucleant is attached; and contacting a crystallization buffer containing a protein having a protein concentration at the level of no-precipitation occurrence in the crystallization buffer with the nucleant to promote a self-organized crystal packing for crystal nucleation, wherein the nucleant having a lattice distance 0.3 to 3 times the radius of the protein size to be crystallized.

11. The method according to claim 10, wherein the nucleant is attached to a substrate in a state of an aqueous liquid or a coating layer.

12. The method according to claim 10, wherein a crystallization plate having one or more wells is used as the substrate.

13. A crystallization kit for crystallizing a protein, comprising at least a nucleant for crystallizing a protein according to claim 1 and a crystallization plate having one or more wells.

14. The method according to claim 5, wherein the metal complex is a metal complex in which 2,4,6-tris[4-pyridinyl]-1,3,5-triazine or 2,4,6-tris[4-(4-pyridinyl)phenyl]-1,3,5-triazine is coordinated with a cobalt divalent ion, or a metal complex in which 2,4,6-tris[4-pyridinyl]-1,3,5-triazine is coordinated with a zinc divalent ion.

15. The method according to claim 10, wherein the protein is selected from a group consisting of GatCAB, EHEP, Tre6PP, trypsin, rhodopsin, protein1, ychN, protein2, PH0828, Annexin A2, and Lysozyme.

* * * * *